(12) United States Patent
Burnes et al.

(10) Patent No.: US 6,608,236 B1
(45) Date of Patent: Aug. 19, 2003

(54) STABILIZED ABSORBENT MATERIAL AND SYSTEMS FOR PERSONAL CARE PRODUCTS HAVING CONTROLLED PLACEMENT OF VISCO-ELASTIC FLUIDS

(75) Inventors: Andrew Scott Burnes, Lawrenceville, GA (US); Rebecca Lyn Dilnik, Neenah, WI (US); Connie Lynn Hetzler, Sparta, NJ (US); Thomas Patrick Jorgenson, Neenah, WI (US); Tamara Lee Mace, Doraville, GA (US); David Michael Matela, Alpharetta, GA (US); Jayne Bramstedt Nelson, Neenah, WI (US); Lawrence Howell Sawyer, Roswell, GA (US); Alexander Manfred Schmidt-Foerst, Appleton, WI (US); Heather Anne Sorebo, Appleton, WI (US); James Allyn Spiers, Acworth, GA (US); Laura Jane Walker, Appleton, WI (US); Rodney Lawrence Abba, Oshkosh, WI (US); Charles John Chappell, Menasha, WI (US); Valerie Victoria Finch, Neenah, WI (US); Ann Marie Giencke, Menasha, WI (US); Michael Brent Kottek, Neenah, WI (US); Allan James Krueger, Winneconne, WI (US); Andrew Michael Lake, Combined Locks, WI (US); MeeWha Lee, Appleton, WI (US); Sarah Elizabeth Long-Radloff, Appleton, WI (US); Janice Gail Nielsen, Appleton, WI (US); Ann Margaret Vanevenhoven, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 297 days.

(21) Appl. No.: 09/072,172

(22) Filed: May 5, 1998

Related U.S. Application Data

(60) Provisional application No. 60/079,657, filed on Mar. 27, 1998, provisional application No. 60/046,701, filed on May 14, 1997, and provisional application No. 60/046,480, filed on May 14, 1997.

(51) Int. Cl.$^7$ .............................................. A61F 13/15
(52) U.S. Cl. .................................. 604/378; 604/385.01
(58) Field of Search ............................. 604/378, 385.01

(56) References Cited

U.S. PATENT DOCUMENTS 3,338,992 A  8/1967  Kinney ........................ 264/24

(List continued on next page.)

FOREIGN PATENT DOCUMENTS

DE  25 13 251  9/1976  ............. D01F/8/08

(List continued on next page.)

OTHER PUBLICATIONS

*Polymer Blends and Composites* by John A. Manson and (List continued on next page.)

*Primary Examiner*—Dennis Ruhl
(74) *Attorney, Agent, or Firm*—James B. Robinson; Steven D. Flack

(57) ABSTRACT

There is provided a distribution material for personal care products which is a fabric which wicks artificial menses according to a horizontal wicking test a distance of about 1 inch in less than about 1.5 minutes. Materials meeting this performance criteria generally have a pore size distribution with a high percentage (usually more than 50 percent) of pore diameters between about 80 and 400 microns and a density below about 0.15 g/cc.

There is also provided a personal care product system having a distribution/retention layer and a pad shaping layer wherein each layer has a stain length ratio of 0.5 or less and the distribution/retention layer has a saturation profile of 4 or less.

20 Claims, 11 Drawing Sheets

U.S. PATENT DOCUMENTS

| | | | |
|---|---|---|---|
| 3,341,394 A | 9/1967 | Kinney | 161/72 |
| 3,502,763 A | 3/1970 | Hartmann | 264/210 |
| 3,542,615 A | 11/1970 | Dobo et al. | 156/181 |
| 3,692,618 A | 9/1972 | Dorschner et al. | 161/72 |
| 3,802,817 A | 4/1974 | Matsuki et al. | 425/66 |
| 3,849,241 A | 11/1974 | Butin et al. | 161/169 |
| 4,005,957 A | 2/1977 | Savich | 425/80 |
| 4,100,324 A | 7/1978 | Anderson et al. | 428/288 |
| 4,340,563 A | 7/1982 | Appel et al. | 264/518 |
| 4,388,056 A | 6/1983 | Lee et al. | 425/83.1 |
| 4,419,403 A | 12/1983 | Varona | 428/288 |
| 4,592,708 A | 6/1986 | Feist et al. | 425/80.1 |
| 4,598,441 A | 7/1986 | Stemmler | 19/145 |
| 4,610,678 A | 9/1986 | Weisman et al. | 604/368 |
| 4,673,402 A | 6/1987 | Weisman et al. | 604/368 |
| 4,674,966 A | 6/1987 | Johnson et al. | 425/82.1 |
| 4,738,676 A | 4/1988 | Osborn, III | 604/385 R |
| 4,761,258 A | 8/1988 | Enloe | 264/518 |
| 4,764,325 A | 8/1988 | Angstadt | 264/113 |
| 4,765,780 A | 8/1988 | Angstadt | 406/123 |
| 4,773,903 A | 9/1988 | Weisman et al. | 604/368 |
| 4,781,710 A | 11/1988 | Megison et al. | 604/378 |
| 4,795,668 A | 1/1989 | Krueger et al. | 428/174 |
| 4,818,464 A | 4/1989 | Lau | 264/510 |
| 4,859,388 A | 8/1989 | Peterson et al. | 264/121 |
| 4,865,596 A | 9/1989 | Weisman et al. | 604/368 |
| 4,888,231 A | 12/1989 | Angstadt | 428/213 |
| 4,904,440 A | 2/1990 | Angstadt | 264/510 |
| 4,908,175 A | 3/1990 | Angstadt | 264/113 |
| 4,935,022 A | 6/1990 | Lash et al. | 604/368 |
| 4,950,264 A | 8/1990 | Osborn, III | 604/385.1 |
| 4,988,344 A | 1/1991 | Reising et al. | 604/368 |
| 5,004,579 A | 4/1991 | Wislinski et al. | 264/517 |
| 5,037,409 A | 8/1991 | Chen et al. | 604/358 |
| 5,057,368 A | 10/1991 | Largman et al. | 428/373 |
| 5,069,970 A | 12/1991 | Largman et al. | 428/373 |
| 5,108,820 A | 4/1992 | Kaneko et al. | 428/198 |
| 5,108,827 A | 4/1992 | Gessner | 428/219 |
| 5,134,007 A | 7/1992 | Reising et al. | 428/78 |
| 5,200,248 A | 4/1993 | Thompson et al. | 428/131 |
| 5,277,976 A | 1/1994 | Hogle et al. | 428/397 |
| 5,294,482 A | 3/1994 | Gessner | 428/287 |
| H1298 H | 4/1994 | Ahr et al. | 428/296 |
| 5,336,552 A | 8/1994 | Strack et al. | 428/224 |
| 5,382,400 A | 1/1995 | Pike et al. | 264/168 |
| 5,383,869 A | 1/1995 | Osborn, III | 604/385.1 |
| 5,387,208 A | 2/1995 | Ashton et al. | 604/378 |
| 5,419,956 A | 5/1995 | Roe | 428/283 |
| 5,422,169 A | 6/1995 | Roe | 428/212 |
| 5,460,622 A | 10/1995 | Dragoo et al. | 604/378 |
| 5,466,232 A | 11/1995 | Cadieux et al. | 604/378 |
| 5,466,410 A | 11/1995 | Hills | 264/172.11 |
| 5,486,167 A | 1/1996 | Dragoo et al. | 604/384 |
| 5,505,718 A | 4/1996 | Roe et al. | 604/368 |
| 5,509,914 A | 4/1996 | Osborn, III | 604/368 |
| 5,531,728 A | 7/1996 | Lash | 604/378 |
| 5,540,992 A | 7/1996 | Marcher et al. | 428/373 |
| 5,549,589 A | 8/1996 | Horney et al. | 604/366 |
| 5,575,786 A | 11/1996 | Osborn, III | 604/387 |
| 5,647,862 A | 7/1997 | Osborn, III et al. | 604/378 |
| 5,681,300 A | 10/1997 | Ahr et al. | 604/367 |

FOREIGN PATENT DOCUMENTS

| | | | |
|---|---|---|---|
| DE | 35 08 344 | 9/1986 | A61F/13/00 |
| EP | 0 359 501 | 3/1990 | A61F/13/15 |
| EP | 0 494 112 | 7/1992 | A61F/13/15 |
| EP | 0 523 683 | 1/1993 | A61F/13/46 |
| GB | 2 191 793 | 12/1987 | D01G/23/08 |
| WO | 94/26221 | 11/1994 | A61F/13/46 |
| WO | 95/17867 | 7/1995 | A61F/13/00 |
| WO | 95/17870 | 7/1995 | A61F/13/15 |
| WO | 96/19171 | 6/1996 | A61F/13/15 |
| WO | 96/40513 | 12/1996 | B32B/27/12 |

OTHER PUBLICATIONS

Leslie H. Sperling, copyright 1976 by Plenum Press, a division of Plenum Publishing Corporation of New York, IBSN 0–306–30831–2, at pp. 273 through 277.

Burgeni and Kapur, The Textile Research Journal, vol. 37(1967), p. 356.

Chatterjee's Absorbency, Elsevier Science Publishers, B.V. 1985, pp. 36–40.

STABILIZED ABSORBENT MATERIAL AND SYSTEMS FOR PERSONAL CARE PRODUCTS HAVING CONTROLLED PLACEMENT OF VISCO-ELASTIC FLUIDS

This application claims priority from U.S. Provisional Applications, Nos. 60/046,701 and 60/046,480 filed May 14, 1997, and 60/079,657 filed Mar. 27, 1998.

FIELD OF THE INVENTION

The present invention concerns a material structure and absorbent structures or systems which are useful in personal care products such as disposable sanitary napkins, diapers, or incontinence guards. More particularly, the invention relates to absorbent systems that must manage complex viscous body liquids like menses fluid.

BACKGROUND OF THE INVENTION

Absorbent articles such as feminine pads or sanitary napkins, diapers and incontinent guards are intended to intake and retain body liquids. Current products have deficiencies in these functions that result in higher than desired leakage levels producing stains on clothing. In addition, current products are not perceived to fully deliver on other consumer attributes such as dryness, fit, comfort and confidence. Many of these attributes are effected by the product liquid management performance. Despite continuing improvements in this field, for example, the introduction of "wings" whereby part of a feminine pad wraps around the wearer's underwear to protect it from leakage, there remains a need for feminine hygiene products with reduced leakage and improved comfort.

Most commercially available pads have relatively high leakage rates. These pads may fail as much as 30 percent of the time, and failure rates of about 20 percent are quite common. Such failures are believed to be due to the highly viscous nature of menses and the great variability in delivery volume which results in overloading of the pad in the target area and subsequent leaking. Insufficient lo distribution of menses is believed to be one of the key causes of the target area overloading.

In the field of urine management in personal care products like diapers, distribution is often provided by materials that have small pores with a narrow pore size distribution. These materials must move the high volume, low viscosity urine insults out of the target area in a time sufficient for the target area to be able to accept the next insult. The movement of urine may be to relatively remote parts of the diaper overcoming substantial hydrostatic pressure. In contrast, feminine hygiene products experience lower total insult volume but the fluid is of greater viscosity, making it more difficult to move the fluid. Distribution materials must be quite different for feminine hygiene products than for products concerned primarily with urine management.

Several examples of improved urine management may be found in U.S. patent application Ser. Nos. 08/754,414 and 08/755,136, commonly assigned, which teach applications of advanced absorbent materials and system designs. While the physics of liquid management is somewhat similar for menses and urine, the complex nature of menses as well as the variability of menses and the product use conditions require significantly different designs for absorbent materials and systems than that required for urine management. Previous attempts to provide lower leakage feminine hygiene products include U.S. Pat. Nos. 5,549,589, 5,466,232 and 5,200,248, which discuss distribution structures for menses. None of these references provide the unique combination of attributes of the instant invention.

It is an object of this invention to provide a feminine hygiene products having superior distribution performance to allow movement of menses from the target area and provide comfort, dry feeling, and lower leakage than traditional pads.

It is an objective of this invention to provide an improved feminine hygiene product which reduces leakage and improves comfort through the use of materials which are designed to accommodate the characteristics of menses and then direct the menses liquid into the absorbent system, substantially isolating it in a localized region of the absorbent system. It is a further object of the invention to provide a feminine hygiene product which has pores which are available and capable of holding adequate amounts of liquid without interfering with intake and distribution.

SUMMARY OF THE INVENTION

The object of the invention is achieved by a distribution material comprised of stabilized, highly wettable fibers arranged to provide capillary pore sizes and a degree of wettability ideally suited to wick visco-elastic fluids. When exposed to a visco-elastic fluid and simulants, these materials demonstrate improved fluid distribution performance in terms of the distance wicked, the wicking rate, as well as the amount of fluid moved.

The distribution material for personal care products of this invention is a fabric which wicks artificial menses according to a horizontal wicking test a distance of about 1 inch in less than about 1.5 minutes. Materials meeting this performance criteria generally have a pore size distribution with a high percentage (usually more than about 50 percent) of pore diameters between about 80 and 400 microns and a density below about 0.15 g/cc.

There is also provided a personal care product system having a distribution/retention layer and a pad shaping layer wherein each layer has a stain length ratio of 0.5 or less and the distribution/retention layer has a saturation profile of 4 or less.

DEFINITIONS

Figure 1:
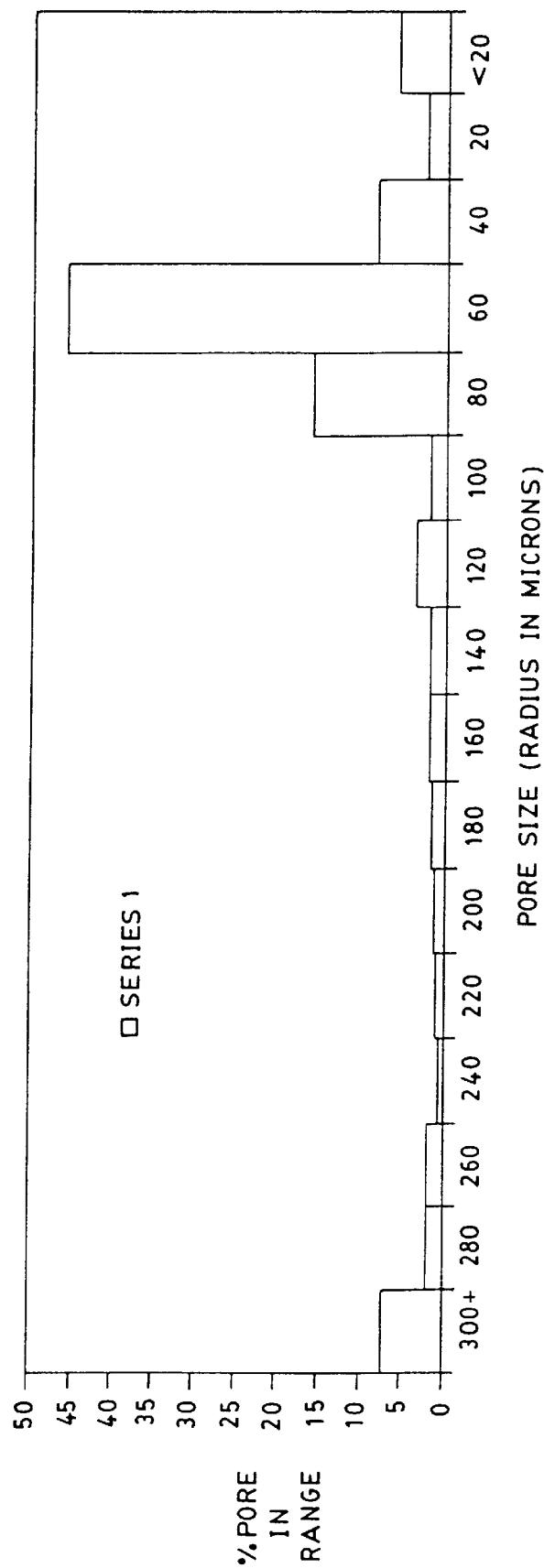
FIG. 1 is a graph of the pore size distribution of the 0.05 g/cc material of Example 1, repetition 1.

"Disposable" includes being disposed of after use and not intended to be washed and reused.

"Front" and "back" are used throughout this description to designate relationships relative to the garment itself, rather than to suggest any position the garment assumes when it is positioned on a wearer.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials can be provided by a Cahn SFA-222 Surface Force Analyzer System, or a substantially equivalent system. When measured with this system, fibers having contact angles less than 90° are designated "wettable" or hydrophilic, while fibers having contact angles equal to or greater than to 90° are designated "nonwettable" or hydrophobic.

"Inward" and "outward" refer to positions relative to the center of an absorbent garment, and particularly transversely and/or longitudinally closer to or away from the longitudinal and transverse center of the absorbent garment.

"Layer" when used in the singular can have the dual meaning of a single element or a plurality of elements.

"Liquid" means a substance and/or material that flows and can assume the interior shape of a container into which it is poured or placed.

"Liquid communication" means that liquid is able to travel from one layer to another layer, or one location to another within a layer.

"Longitudinal" and "transverse" have their customary meaning. The longitudinal axis lies in the plane of the article when laid flat and fully extended and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Particles" refers to any geometric form such as, but not limited to, spherical grains, cylindrical fibers or strands, flat surfaces or roughened surfaces, sheets, ribbons, strings, strands, or the like.

"Spray" and variations thereof include forcefully ejecting liquid, either as a stream or, such as swirl filaments, or atomized particles through an orifice, nozzle, or the like, by means of an applied pressure of air or other gas, by force of gravity, or by centrifugal force. The spray can be continuous or non-continuous.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns. The fibers may also have shapes such as those described in U.S. Pat. Nos. 5,277,976 to Hogle et al., U.S. Pat. No. 5,466,410 to Hills and U.S. Pat. Nos. 5,069,970 and 5,057,368 to Largman et al., which describe fibers with unconventional shapes.

As used herein the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited onto a collecting surface.

As used herein, the term "coform" means a process in which at least one meltblown diehead is arranged near a chute through which other materials are added to the web while it is forming. Such other materials may be pulp, superabsorbent particles, natural polymers (for example, rayon or cotton fibers) and/or synthetic polymers (for example, polypropylene or polyester) fibers, for example, where the fibers may be of staple length. Coform processes are shown in commonly assigned U.S. Pat. No. 4,818,464 to Lau and U.S. Pat. No. 4,100,324 to Anderson et al. Webs produced by the coform process are generally referred to as coform materials.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the molecule. These configurations include, but are not limited to isotactic, syndiotactic and random symmetries.

As used herein, the term "machine direction" or MD means the length of a fabric in the direction in which it is produced. The term "cross machine direction" or CD means the width of fabric, i.e. a direction generally perpendicular to the MD.

As used herein the term "monocomponent" fiber refers to a fiber formed from one or more extruders using only one polymer. This is not meant to exclude fibers formed from one polymer to which small amounts of additives have been added for coloration, anti-static properties, lubrication, hydrophilicity, etc. These additives, e.g. titanium dioxide for coloration, are generally present in an amount less than 5 weight percent and more typically about 2 weight percent.

As used herein the term "conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat. No. 4,795,668 to Krueger et al., U.S. Pat. No. 5,540,992 to Marcher et al. and U.S. Pat. No. 5,336,552 to Strack et al. Conjugate fibers are also taught in U.S. Pat. No. 5,382,400 to Pike et al. and may be used to produce crimp in the fibers by using the differential rates of expansion and contraction of the two (or more) polymers. Crimped fibers may also be produced by mechanical means and by the process of German Patent DT 25 13 251 A1. For two component fibers, the polymers may be present in ratios of 75/25, 50/50, 25/75 or any other desired ratios. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., which describe fibers with unconventional shapes.

As used herein the term "biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. Nos. 5,108,827 and 5,294,482 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, IBSN 0-306-30831-2, at pages 273 through 277.

As used herein the term "blend" means a mixture of two or more polymers while the term "alloy" means a sub-class of blends wherein the components are immiscible but have been compatibilized. "Miscibility" and "immiscibility" are defined as blends having negative and positive values, respectively, for the free energy of mixing. Further, "compatibilization" is defined as the process of modifying the interfacial properties of an immiscible polymer blend in order to make an alloy.

"Bonded carded web" refers webs are made from staple fibers which are sent through a combing or carding unit, which breaks apart and aligns the staple fibers in the machine direction to form a generally machine direction-oriented fibrous nonwoven web. Such fibers are usually purchased in bales which are placed in a picker which separates the fibers prior to the carding unit. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well-known bonding method, particularly when using bicomponent staple fibers, is through-air bonding.

"Airlaying" is a well known process by which a fibrous nonwoven layer can be formed. In the airlaying process, bundles of small fibers having typical lengths ranging from about 6 to about 19 millimeters (mm) are separated and entrained in an air supply and then deposited onto a forming screen, usually with the assistance of a vacuum supply. The randomly deposited fibers then are bonded to one another using, for example, hot air or a spray adhesive.

"Personal care product" means diapers, training pants, absorbent underpants, adult incontinence products, bandages and feminine hygiene products.

TEST METHODS

Material caliper (thickness) The caliper of a material is a measure of thickness and is measured at 0.05 psi with a Starret-type bulk tester, in units of millimeters.

Density The density of the materials is calculated by dividing the weight per unit area of a sample in grams per square meter (gsm) by the bulk of the sample in millimeters (mm) at 68.9 Pascals and multiplying the result by 0.001 to convert the value to grams per cubic centimeter (g/cc). A total of three samples would be s evaluated and averaged for the density values.

Wicking Time and Horizontal Liquid Flux of an Absorbent Structure A sample strip of material approximately 1 inch (2.5 cm) by 8 inches (20 cm) is placed horizontally such that when the sample strip is positioned in a liquid reservoir at the beginning of the test, the sample strip will just touch the liquid surface. The relative humidity should be maintained at about 90 to about 98 percent during the evaluation. The sample strip is placed next to an large (effectively infinite) amount of liquid and a stopwatch started as soon as the edge of the sample strip touches the surface of the solution.

The horizontal distance of the liquid front traveling along the sample strip and the liquid weight absorbed by the sample strip at various times is recorded. The weight of the liquid absorbed by the sample strip from the beginning of the evaluation to about a half inch (1.3 cm), 1 inch, 2 inches (5 cm) and 3 inches (7.6 cm) is also determined from the data. The liquid used in this testing was a fluid designed to simulate the visco-elastic and other properties of menses and was made according to the procedure given in the following testing procedure.

Flat System Testing Procedure

Purpose: To determine the fluid handling characteristics of various absorbent systems through analysis of stain length, saturation capacity, and fluid loading of the system components.

Equipment: Hourglass-shaped acrylic plates (with a 0.25 in, hole in the center) weighing approximately 330 grams;

syringes; ⅛ in. I.D. Tygon tubing; pipette pump; menses simulant; laboratory balance (accurate to 0.00 g).

Preparation: 1. Cut components to desired shape (currently 1.5 in. by 5.5 in. for intake and distribution layer; 1.75 in. by 5.5 in. for transfer delay layer; 200 mm long hourglass shape for perimeter layer)

2. Mark 5.5 in. layers into 1.1 in. sections and the perimeter layer into sections corresponding to the marks on the strips when they are centered on the perimeter layer.
3. Weigh each component and record the weight.
4. Assemble the individual components into the desired component system keeping the marked sections aligned. Label one end as the top.
5. Fill the syringes with menses simulant and attach Tygon tubing to syringes.
6. Place syringes in pipette pump.
7. Program pump (currently using 30 cc syringes dispensing 10 ml of simulant in one hour).
8. With the open ends of the tubing placed in a beaker, prime tubing by running pump until all air is out of tubing and simulant is exiting the tubing at the insult end.
9. Place the component systems to be tested near the pipette pump, place a 2 in. by 6 in. (approximately) piece of 25 gsm, 10d BCW on top of the center of the system, and place an acrylic plate centered on top of the system.
10. Insert the free end of one tubing into the hole in the acrylic plate. Repeat for the remaining systems to be tested.
11. Start the pipette pump to begin the insult.
12. At the end of the insult period, remove the tubing and acrylic plates. Carefully remove the BCW (without moving the underlying layers) and discard it.
13. Take photos of the component system and layers and print.
14. Weigh each layer individually and record the weight.
15. Beginning at the end labeled as the top, cut and weigh the first marked section and record the weight. Repeat for the remaining sections and layers.
16. Measure and record the stain length for each layer.
17. Enter the data in a spreadsheet for graphing and analysis.

The menses simulant used in this test was made according to the following procedure:

Blood, in this case defibrinated swine blood, was separated by centrifugation at 3000 rpm for 30 minutes, though other methods or speeds and times may be used if effective. The plasma was separated and stored separately, the buffy coat removed and discarded and the packed red blood cells stored separately as well.

Eggs, in this case jumbo chicken eggs, were separated, the yolk and chalazae discarded and the egg white retained. The egg white was separated into thick and thin portions by straining the white through a 1000 micron nylon mesh for about 3 minutes, and the thinner portion discarded. Note that alternative mesh sizes may be used and the time or method may be varied provided the viscosity is at least that required. The thick portion of egg white which was retained on the mesh was collected and drawn into a 60 cc syringe which was then placed on a programmable syringe pump and homogenized by expelling and refilling the contents five times. In this case, the amount of homogenization was controlled by the syringe pump rate of about 100 ml/min, and the tubing inside diameter of about 0.12 inches. After homogenizing the thick egg white had a viscosity of at least 20 centipoise at 150 $sec^{-1}$ and was then placed in the centrifuge and spun to remove debris and air bubbles at about 3000 rpm for about 10 minutes, though any effective method to remove debris and bubbles may be used.

After centrifuging, the thick, homogenized egg white, which contains ovamucin, was added to a 300 cc Fenwal® Transfer pack using a syringe. Then 60 cc of the swine plasma was added to the transfer pack. The transfer pack was clamped, all air bubbles removed, and placed in a Stomacher lab blender where it was blended at normal (or medium) speed for about 2 minutes. The transfer pack was then removed from the blender, 60 cc of swine red blood cells were added, and the contents mixed by hand kneading for about 2 minutes or until the contents appeared homogenous. A hematocrit of the final mixture showed a red blood cell content of about 30 weight percent and generally should be at least within a range of 28–32 weight percent for artificial menses made according to this example. The amount of egg white was about 40 weight percent.

The ingredients and equipment used in the preparation of this artificial menses are readily available. Below is a listing of sources for the items used, though of course other sources may be used providing they are approximately equivalent.

Blood (swine): Cocalico Biologicals, Inc., 449 Stevens Rd., Reamstown, Pa. 17567, (717) 336-1990.

Fenwal® Transfer pack container, 300 ml, with coupler, code 4R2014: Baxter Healthcare Corporation, Fenwal Division, Deerfield, Ill. 60015.

Harvard Apparatus Programmable Syringe Pump model no. 55-4143: Harvard Apparatus, South Natick, Mass. 01760.

Stomacher 400 laboratory blender model no. BA 7021, serial no. 31968: Seward Medical, London, England, UK.

1000 micron mesh, item no. CMN-1000-B: Small Parts, Inc., PO Box 4650, Miami Lakes, Fla. 33014-0650, 1-800-220-4242 .

Hemata Stat-II device to measure hemocrits, serial no. 1194Z03127: Separation Technology, Inc., 1096 Rainer Drive, Altamont Springs, Fla. 32714.

Pore size distribution The pore size distribution of a material is measured by using an apparatus based on the porous plate method used by Burgeni and Kapur in The Textile Research Journal, volume 37(1967), at p. 356. Using this apparatus, the amount of fluid desorbed from the sample material at various pressures can be correlated to the radius of the pores within the given material. This process is described in Chattterjee's Absorbency, Elsevier Science Publishers, B. V. 1985, pp. 36–40.

The modified system used consists of a movable stage interfaced with a programmable stepper motor and an electronic balance controlled by a personal computer. The control program automatically moves the stage to the desired height, collects data at a specified sampling rate until equilibrium is reached, and then moves to the next calculated height. A Plexiglas® support structure is used to maintain the material/porous plate in a level, upright position throughout the entire test. Controllable parameters of the method include sampling rates, criteria for equilibrium, and pore size range measured. Data for these tested materials were collected using mineral oil (o.82 g/cc, 32 dyne-cm, 0° fluid contact angle) as the test fluid. At the beginning of each test the sample material is placed on the porous plate and then the sample is completely saturated by lowering the porous plate structure. Pore size is then determined by gathering mass data as the pressure (i.e. height of the stage) increases. Equilibrium is established if after 4 intervals of 60 seconds, there was less than 0.05 grams/min change.

Data is presented as percent pore volume vs. pore radius in microns by plotting the pore size on the x-axis and the incremental change in mass divided by the overall change in mass on the y-axis.

DETAILED DESCRIPTION

This invention is a class of distribution materials composed of stabilized, highly wettable fibers arranged to provide capillary pore sizes and a degree of wettability ideally suited to wick visco-elastic fluids. Stabilization may be accomplished by the use of liquid binders, binder fibers, thermally, or in any other method known to those skilled in the art. When exposed to a visco-elastic fluid or fluid simulant, these materials demonstrate improved fluid distribution performance for distance wicked, wicking rate and amount of fluid moved. The pore characteristics are stable whether dry or wet with minimal, preferably less than about 25 percent, more particularly 20 percent and still more particularly 15 percent, swelling or collapse when wetted with the visco-elastic fluid simulant. All of these properties are critical to the overall performance of distribution materials placed in the target area of personal care products like feminine pads.

The caliper (in inches) of the materials measured in a dry state and wet, i.e., after saturation with the menses simulant, using a compressometer at 0.02 psi with a 2 inch diameter foot are shown below:

| Basis weight (gms) | Density (g/cc) | Pulp/binder Percentage | Dry Caliper | Wet Caliper | Collapse |
|---|---|---|---|---|---|
| 100 | 0.06 | 90/10 | 0.075 | 0.069 | 0.006 |
|  |  |  | 0.077 | 0.065 | 0.012 |
|  |  |  | 0.078 | 0.067 | 0.011 |
|  |  | avg. | 0.077 | 0.067 | 0.010 |
| 100 | 0.10 | 90/10 | 0.059 | 0.054 | 0.005 |
|  |  |  | 0.062 | 0.060 | 0.002 |
|  |  |  | 0.064 | 0.056 | 0.008 |
|  |  | avg. | 0.062 | 0.057 | 0.005 |
| 200 | 0.08 | 90/10 | 0.109 | 0.091 | 0.018 |
|  |  |  | 0.110 | 0.098 | 0.012 |
|  |  |  | 0.103 | 0.095 | 0.008 |
|  |  | avg. | 0.107 | 0.095 | 0.013 |
| 200 | 0.20 | 90/10 | 0.046 | 0.052 | -.006 |
|  |  |  | 0.050 | 0.047 | 0.003 |
|  |  |  | 0.042 | 0.044 | -.002 |
|  |  | avg. | 0.046 | 0.048 | -.002 |

Fluid distribution capability requires the appropriate capillary pore structure within a specified range of wettability for the fluid of interest. Distribution materials were developed using several technology approaches that demonstrate the underlying material characteristics needed for favorable performance. Examples of such materials follow.

EXAMPLE 1

In this example, the distribution material consists of about 80 weight percent fluff pulp (Rayonier R-9401 mercerized southern softwood roll pulp) and about 20 weight percent Danaklon short cut (5 mm) 2.2 denier polyethylene/polypropylene (PE/PP) sheath/core conjugate binder fiber with an S2/B2/39 finish. This finish is advertised as remaining hydrophilic after repeated insults. The material was produced at three different densities; 0.05 g/cc, 0.1 g/cc and 0.2 g/cc at a basis weights of about 100 to 250 gsm. Examples of 0.05 g/cc, 0.1 g/cc and 0.2 g/cc materials at a basis weight of about 125 gsm are shown for comparison.

The materials were tested according to the Horizontal Wicking Test which was repeated for a total of three tests using 1 inch by 8 inch samples. Table 1 shows the results where weight is given in grams of retained fluid, time in seconds is and DNR means did not reach.

The fluff pulp was from Rayonier Inc. of Jessup, Ga. 31545. The binder fibers were from Danaklon a/s, located at Engdraget 22, KD-6800 Varde, Denmark, and were 2.2 denier conjugate PE/PP sheath/core fibers cut into 5 mm lengths.

Figure 2:
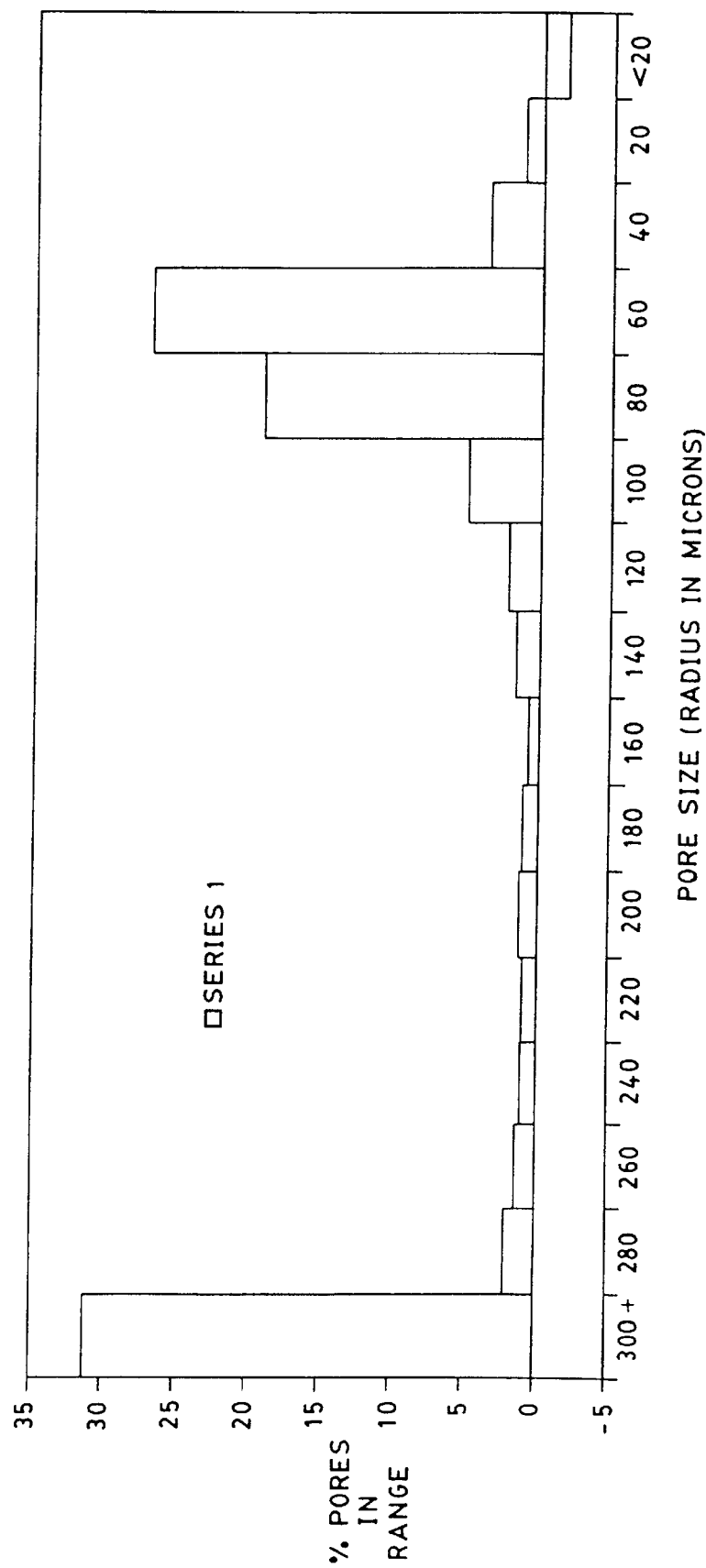
FIG. 2 is a graph of the pore size distribution of the 0.05 g/cc material of Example 1, repetition 2.
Figure 3:
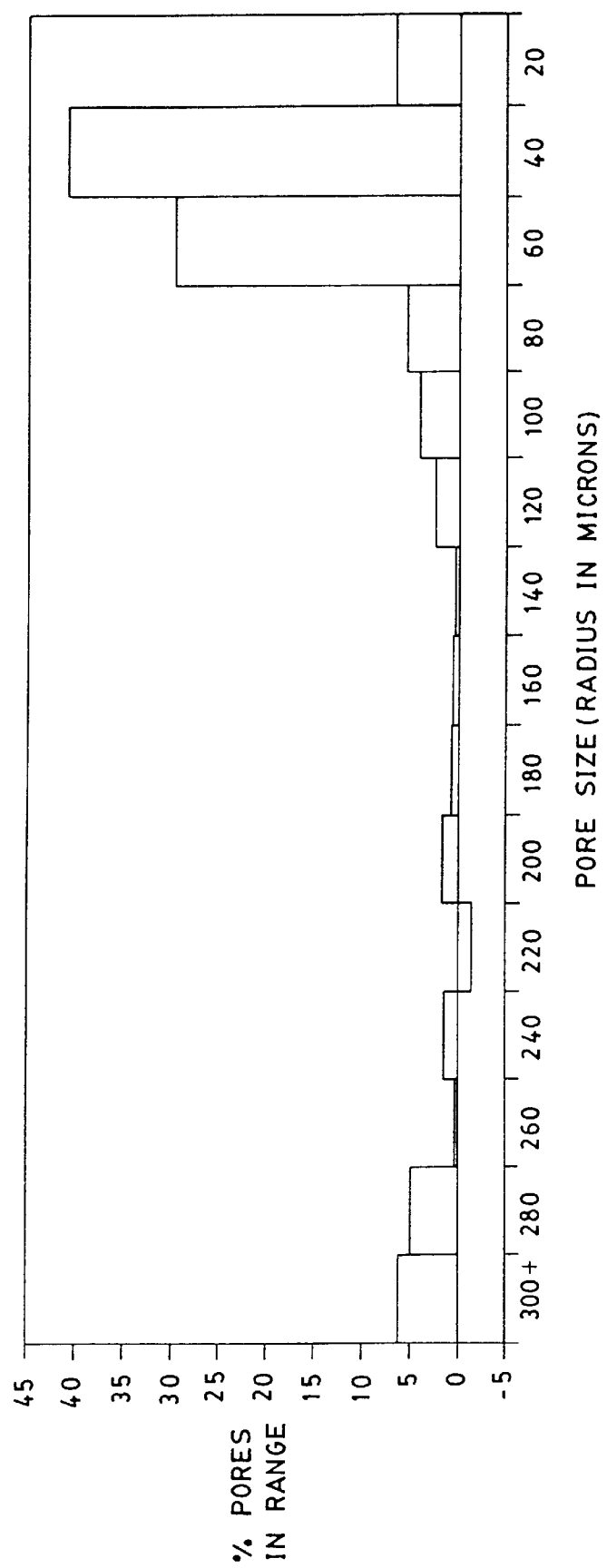
FIG. 3 is a graph of the pore size distribution of the 0.1 g/cc material of Example 1, repetition 1.

The distribution material was produced by the Dan-Web airlaying process. Any other satisfactory procedure known to those skilled in art may be used to produce the material. Some of the samples were tested for pore volume distribution. The results are shown graphically in FIGS. 1, 2 and 3 which show the pore volume distribution for the 0.05 g/cc repetition 1, repetition 2 and the 0.1 g/cc repetition 2. The results show that as density is lowered and pore size is increased, wicking performance is greatly improved.

|  |  | Rep 1 | | Rep 2 | | Rep 3 | |
|---|---|---|---|---|---|---|---|
|  | (inches) | Wt. (g) | Time(s) | Wt. (g) | Time(s) | Wt. (g) | Time(s) |
| 0.05 g/cc | 0.5 | 1.26 | 50 | 1.15 | 50 | 1.13 | 54 |
|  | 1.0 | 1.80 | 161 | 1.77 | 170 | 1.55 | 170 |
|  | 2.0 | 1.56 | 633 | 1.71 | 611 | 1.48 | 714 |
|  | 3.0 | 1.02 | DNR | 0.89 | DNR | 0.72 | DNR |
| 0.1 g/cc | 0.5 | 0.86 | 20 | 0.68 | 24 | 0.76 | 18 |
|  | 1.0 | 1.14 | 155 | 1.07 | 123 | 1.03 | 139 |
|  | 2.0 | 0.95 | 811 | 0.91 | 868 | 0.9 | 810 |
|  | 3.0 | 0.32 | DNR | 0.16 | DNR | 0.23 | DNR |
| 0.2 g/cc | 0.5 | 0.79 | 56 | 0.83 | 43 | 0.73 | 56 |
|  | 1.0 | 1.11 | 253 | 1.03 | 174 | 0.98 | 245 |
|  | 2.0 | 0.62 | DNR | 0.96 | 1074 | 0.76 | DNR |
|  |  |  |  | 0.21 | DNR |  |  |

EXAMPLE 2

Figure 4:
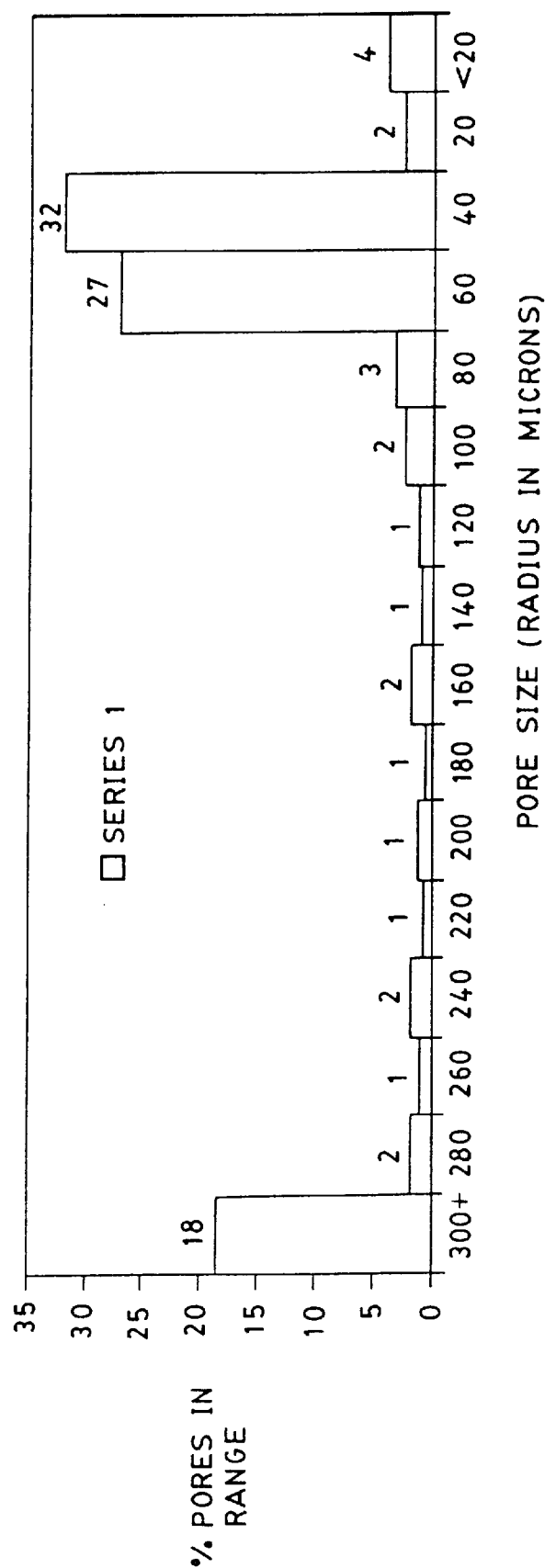
FIG. 4 is a graph of the pore size distribution of the 0.1 g/cc material of Example 1, repetition 2.
Figure 5:
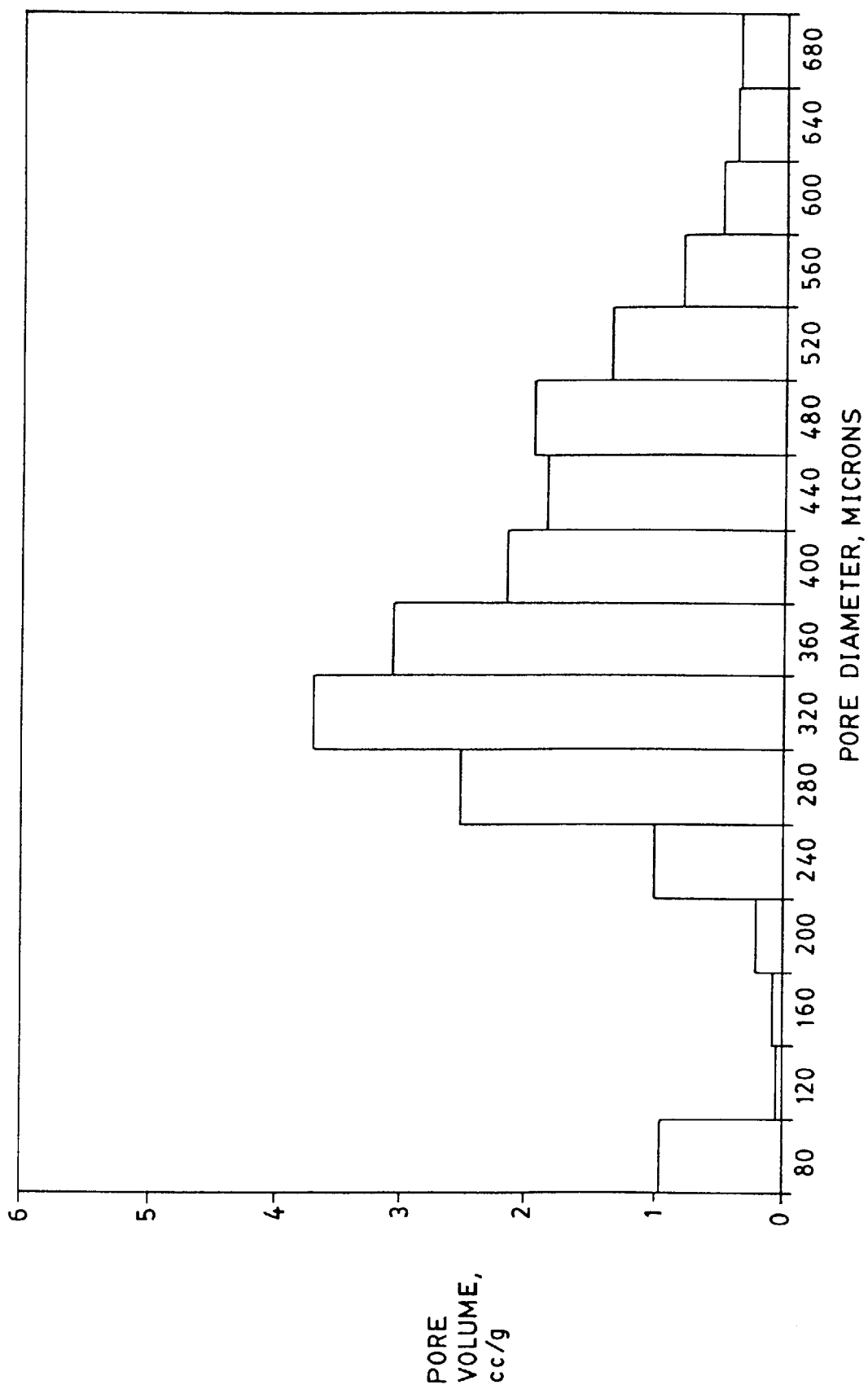
FIG. 5 is a graph of the pore size distribution of the unoriented 0.028 g/cc material of Example 2.
Figure 6:
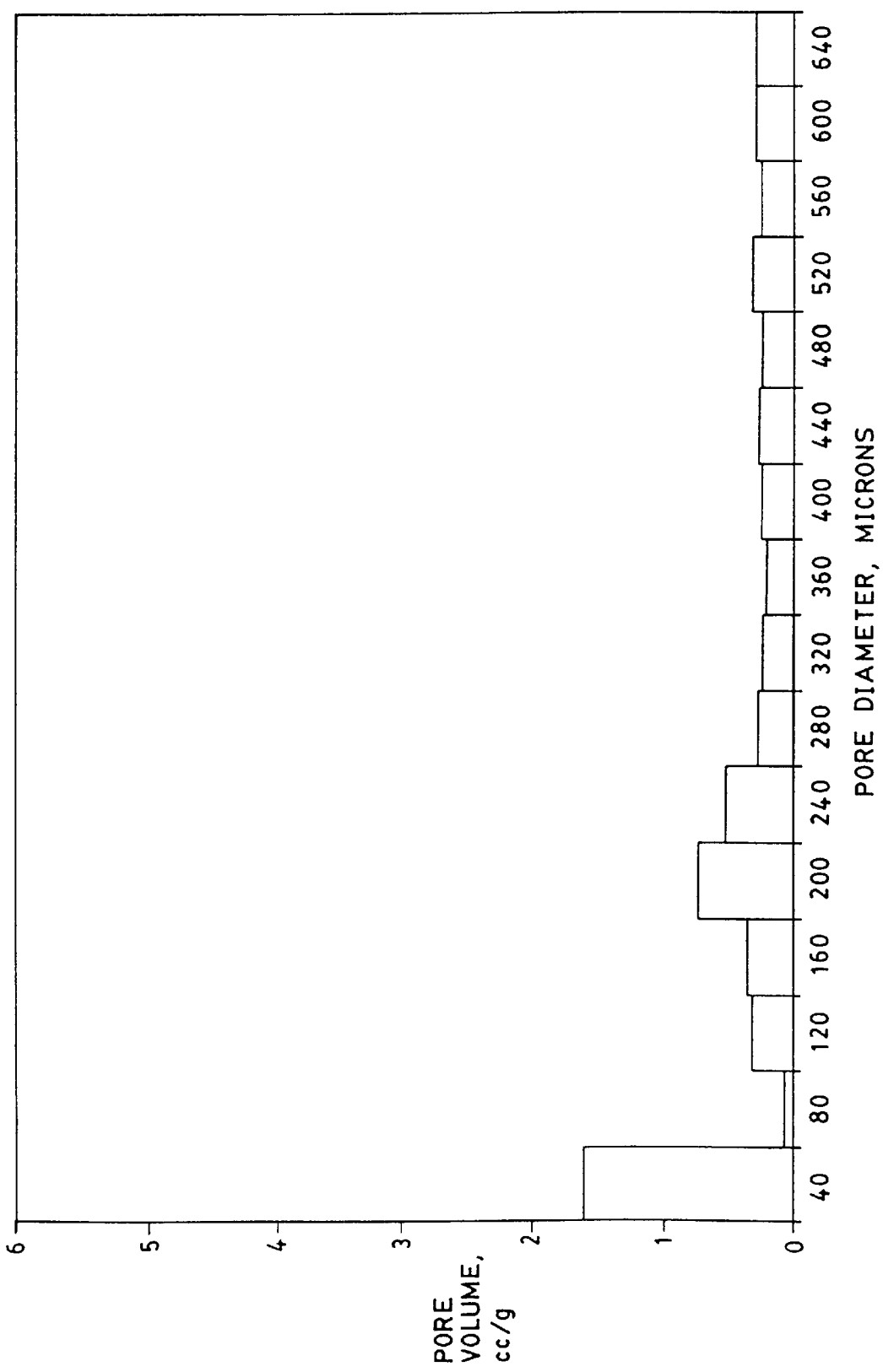
FIG. 6 is a graph of the pore size distribution of the 0.068 g/cc material of Example 2.
Figure 7:
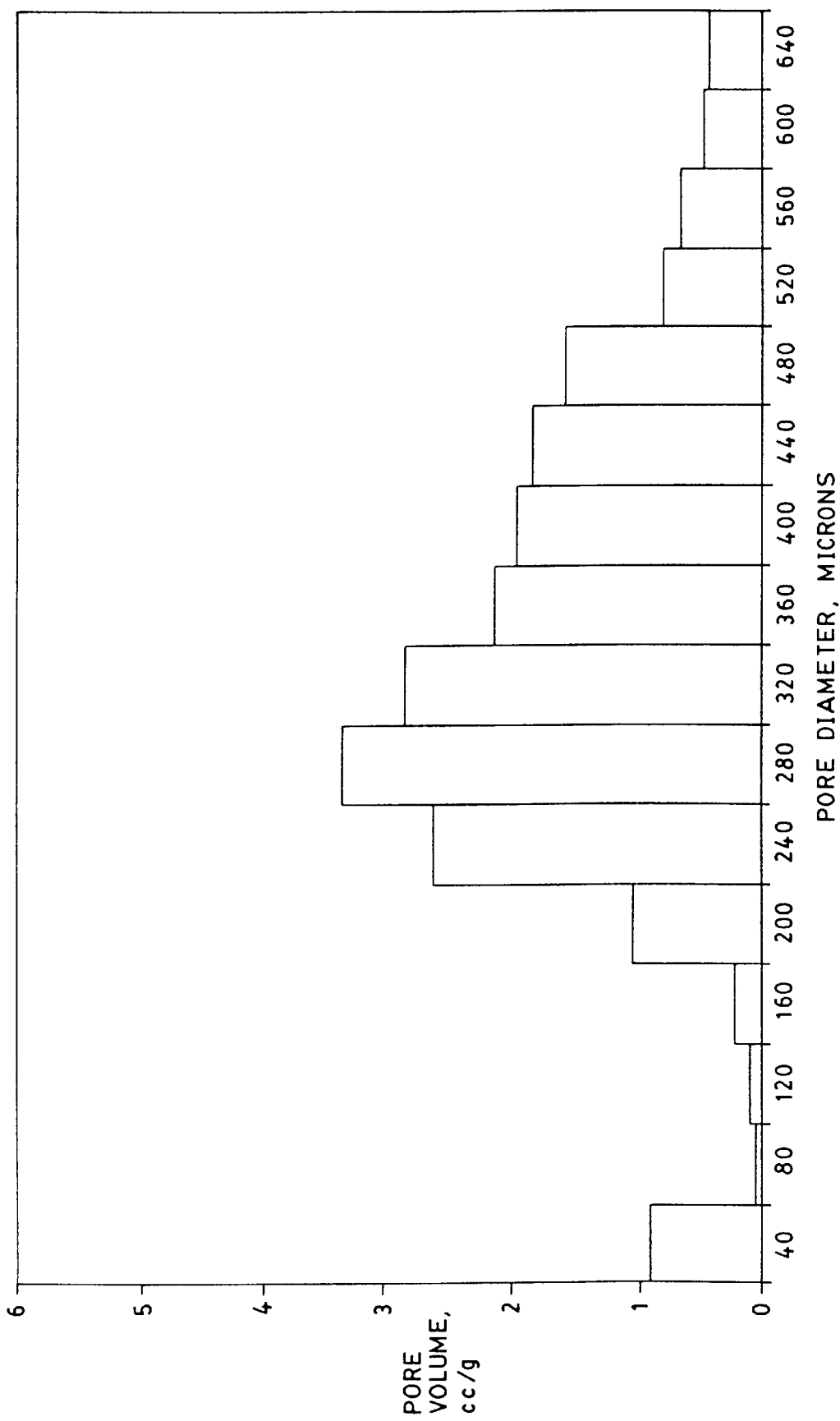
FIG. 7 is a graph of the pore size distribution of the oriented 0.028 g/cc material of Example 2.

In this example, the distribution materials are bonded carded webs consisting of 100 weight percent eccentric sheath/core conjugate fibers of polyethylene and polypropylene available from the Chisso Chemical Co. of Japan. The fibers had a finish known as HR6 applied to them. The table below shows the wicking results for a 0.028 g/cc sample, a 0.068 g/cc sample and a 0.028 g/cc sample in which the fibers were oriented in the carding process. In the table below, the distance is given in inches, the weight in grams and the time in minutes and seconds as indicated. The pore volume distribution was tested and the results are shown in FIGS. 4, 5 and 6 respectively. This data shows that when a high percentage of the pore volume has pores that range from about 200 to about 400 microns, better wicking results are achieved.

| Density | Distance | Weight | Time |
|---|---|---|---|
| 0.028 g/cc | 1.0 | 1.7 | 50 sec. |
|  | 2.0 | 1.1 | 10 min. |
|  | 3.0 | 0.9 | 17 min. |
| 0.068 g/cc | 1.0 | 0.6 | 1.5 min. |
|  | 2.0 | 0.1 | DNR |
| 0.028 g/cc oriented | 1.0 | 1.7 | 1 min. |
|  | 2.0 | 1.2 | 6.6 min. |
|  | 3.0 | 0.9 | 18 min. |
|  | 4.0 | 0.1 | 20 + min. |

The distribution material of this invention should wick the artificial menses fluid according to the horizontal wicking test a distance of an inch (2.5 cm) in less than about 1.5 minutes to be successful. Materials meeting this performance criteria generally have a pore size distribution with a high percentage (usually more than 50 percent, more particularly more than 60 percent and still more particularly more than 70 percent) of pore diameters between about 80 and 400 microns and a density below about 0.15 g/cc. Its believed that increasing the wettability of the pore surface results in greater wicking driving forces which can maintain liquid movement in smaller pores with higher resistive forces.

Figure 8:
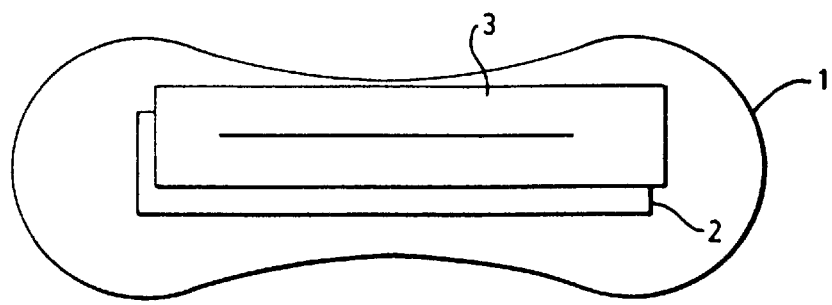
FIG. 8 shows a multiple layered design.

The personal care product system of this invention has been designed to have controlled final liquid storage in a centralized region along the length of the pad. This functional behavior is highly desirable for preventing side leakage which is a dominant form of leakage for feminine pads. The storage behavior is achieved by a layered absorbent design that can include three or more layers. The bottom-most layer, i.e., the layer farthest from a wearer, has larger x-y dimensions than the other layers that are on top of it. This creates a raised topography design that increases the probability that menses from the wearer will land on the narrow strip as shown in FIG. 8. FIG. 8 shows a multiple layered design having a bottom-most layer 1, a top or intake layer 3 and an intermediate layer 2.

The pores in each material layer are designed in combination with the geometry of the layers to cause a specific controlled filling strategy in the absorbent system. The average pore size of the second or middle layer is smaller than the average pore size in both the top and bottom layers. Its believed, therefore, that the fluid is attracted to and distributed by the middle layer. The average pore size of the bottom layer is larger than the middle layer, which is believed to inhibit fluid from transferring to the bottom layer early in the life of the product. This reduction of fluid in the bottom layer is critical for reducing leakage because its believed that any fluid in this, the widest layer, can begin to wick to the edge and cause side leakage. In addition, each layer is stabilized to help maintain the intended pore size relationship throughout its use in addition to having the microscopic integrity required for pad shaping.

In an alternative embodiment, the bottom layer can have an embossed or densified section such as longitudinal lines that help to keep fluid down the center of the bottom layer if high saturation levels cause transfer from the middle layer to bottom layer, such as may happen late in the life of the product.

The top layer, also called the intake layer is the layer closest to a wearer and has a low density; ranging from about 0.02–0.06 g/cc, and a basis weight from about 25 gsm to about 125 gsm. This results in pore sizes ranging from 80 microns to 1000 microns in diameter which are well suited to intake viscous menses fluid.

The top or intake layer can be produced with a range of technologies. Nonexclusive examples include 100 weight percent synthetic fibers in a bonded carded web or an airlaid mixture of cellulosic and synthetic binder fibers.

The layer below the top layer is designed to distribute and retain fluid and so is called the distribution/retention layer or strip. It has a density range from about 0.1 g/cc to about 0.2 g/cc but must be a higher density than the intake layer. This increased density is believed to help desorb the intake layer into the distribution/retention layer. The distribution/retention layer should have a basis weight from about 175 gsm to about 300 gsm and have an average pore size of about 40–500 $\mu$m in diameter. Materials suitable for this layer include airlaid materials that blend high levels of cellulosic fibers (80–95 weight percent) with synthetic binder fibers (5–20 weight percent) which stabilize the web performing this distribution function, provided, however, that the fibers that make up this layer be highly wettable.

The bottom or pad shaping layer has a lower density than the distribution/retention layer. Its primary function is to facilitate body fit, provide comfort to the wearer, and to provide additional coverage. Its density ranges from about 0.03 g/cc to about 0.10 g/cc, so it does not readily desorb the distribution/retention layer, resulting in most fluid remaining in the distribution/retention layer. In some designs, the pad shaping layer can be an airlaid web with 80–90 weight percent cellulosic pulp fluff blended with 10–20 weight percent synthetic binder fiber. While its primary purpose is pad shaping, this layer can accept liquid from the distribution/retention strip especially when the distribution/retention strip is highly loaded with liquid. This pad shaping layer can also include embossing patterns such as lines, sine waves, acorns, etc.

An additional aspect of the invention is a pad shaping feature wherein the uppermost two (intake and distribution/retention) layers may be longitudinally (lengthwise) slit, preferably in the center, to allow them to bend when the bottom layer begins to experience side compression. This creates a close to body fit which is also critical for leakage reduction.

It should be noted that though the invention is referred to as having "layers" this does not mean that separate materials must be produced and laminated together. The term "layers" is meant to also include a single monolithic material wherein the properties vary within it in such a manner as to satisfy the functional and physical characteristics of this invention. Thus a material produced in a single step process and having, for example, characteristics varying from top to bottom regions in such a way as to satisfy the requirements of the invention, is contemplated to be within the claims. A discussion of such a material may be found in a co-assigned patent application, filed the same day as this application under attorney docket number 14002.

Figure 9:
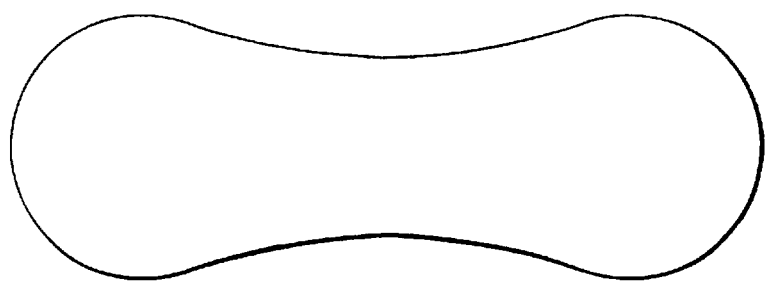
FIG. 9 shows an example of a cover material.
Figure 10:
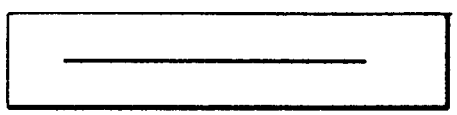
FIG. 10 shows an intake layer.
Figure 11:
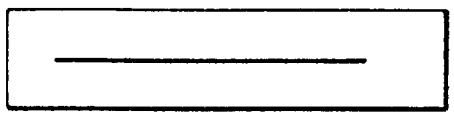
FIG. 11 shows a distribution/retention layer.
Figure 12:
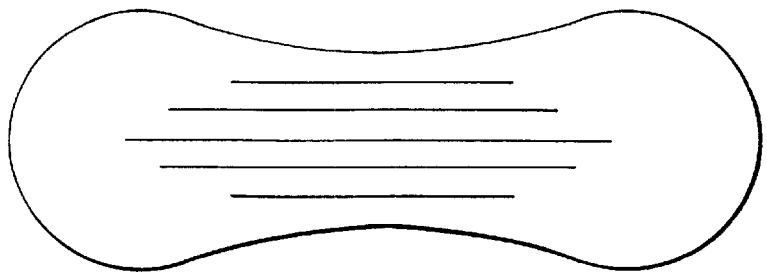
FIG. 12 shows a bottom or pad shaping layer.

The invention can be modified into various forms in order to provide the functional benefits for a wide range of product forms. FIGS. 9, 10, 11 and 12 illustrate example component arrangements that target very thin designs for users that prefer that type of product form. FIG. 9 shows an example of a cover material which would contact the wearer where the cover is about 80 mm in width in the center, about 90 mm in width at the greatest point, and about 238 mm long. FIG. 10 shows an intake layer which is about 37 mm in width and 218 mm long with a centered slit about 101 mm long. FIG. 11 shows a distribution/retention layer of the same dimensions as the intake layer. FIG. 12 shows a bottom or pad shaping layer in the same general shape as the cover layer but having a width of 60 mm in the center and 70 mm at the largest points. The bottom layer in FIG. 12 has five embossed lines of varying lengths, equidistant and centered on the pad. The layers of FIGS. 10, 11 and 12 are further described in Table 1.

The following examples were produced in order to illustrate the distribution characteristics of the invention.

EXAMPLE 3

Nonwoven fabrics were produced according to the air-laying process from pulp fluff and synthetic binder fiber. Alternative fluffs include Coosa 054, 100 weight percent softwood available from the Kimberly-Clark Corporation, Weyerhaeuser NB416 or NF405 100 weight percent softwood, Rayonier 9401, or any other fluff with similar properties. The synthetic binder fiber was Hoechst-Celanese T-255 (H-C T-255) from 1.8 denier to 3 denier. Any other binder that will impart similar bonding properties to the composite may be used.

The basis weights and densities were as shown in Table 1.

TABLE 1

| FIG. | Function | Composition | Basis Weight | Density |
|---|---|---|---|---|
| 10 | Intake | Airlaid 90/10 Fluff/Binder | 100 gsm | 0.1 g/cc |
| 11 | Distribution/ Retention | Airlaid 90/10 Fluff/Binder | 200 gsm | 0.2 g/cc |
| 12 | Pad Shaping Retention | Airlaid 90/10 Fluff/Binder | 175 gsm | 0.1 g/cc |

EXAMPLE 4

Figure 13:
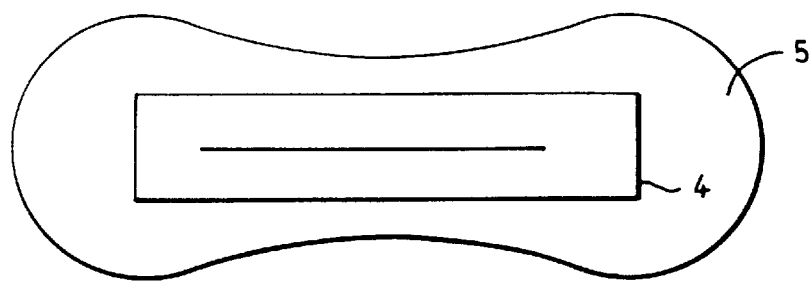
FIG. 13 shows a two layer design for a feminine hygiene product.

Is this two layer design, shown in FIG. 13, the top strip 4 is in a density range that can intake, distribute, and retain the menses liquid. The bottom, or pad shaping layer 5, has a lower density, and therefore inhibits fluid transfer into itself until the top strip is highly saturated. The design preserves the thinness desired by some users. The properties of the layers of the example illustrated in FIG. 13 are as follows.

| Function | Composition | Basis Weight | Density |
|---|---|---|---|
| Intake/Dist/Ret | Airlaid 90/10 | 250 gsm | 0.1 g/c |
| Pad Shaping/Ret | Airlaid 90/10 | 175 gsm | .05 g/cc |

EXAMPLE 5

Figure 14:
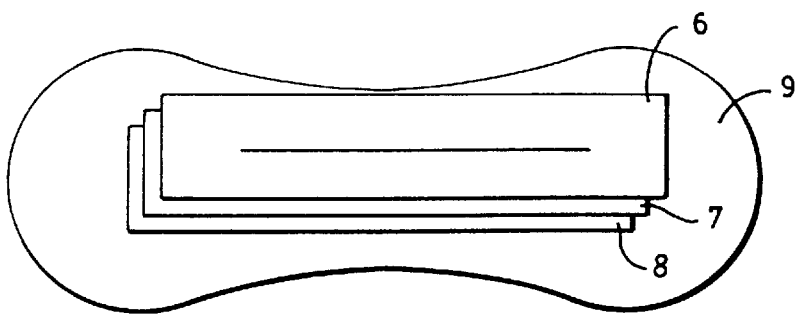
FIG. 14 illustrates a type of four layer design.

In yet another variation, this absorbent system invention can also provide thick products for users that prefer that product form. FIG. 14 illustrates this type of four layer design where the intake layer 6 is above distribution/retention layer 7, which is above transfer delays strip 8 and finally the pad shaping layer 9.

In this example and as shown in FIG. 14, the intake layer 6 provides the intake function while the next layer 7 is a higher density distribution/retention strip. The third layer 8 has a lower density than the distribution retention strip 7 and therefore provides a delay in fluid transferring to the wider and thicker pad shaping layer 9 which also provides comfort and thickness requirements for this range of product forms. Preventing fluid from entering the widest layer reduces the chance of wicking to the edges which causes leakage. Pad shaping layer 9 can have embossing patterns to prevent liquid from wicking to the sides once liquid has penetrated through transfer delay layer 8 late in the life of the product.

While these three examples help illustrate the invention, the invention is not limited to only the examples. The invention includes absorbent articles that maintain a controlled placement of liquid down the center of the absorbent system in order to is prevent side leakage.

The following test data demonstrates this controlled filling pattern for a range of absorbent system examples. In the following discussion, "top layer" refers to the intake layer, "middle layer" refers to the distribution/retention layer, and "bottom layer" refers to the pad shaping layer. The test procedure involves assembling the absorbent system components and insulting them with 10 ml at 10 ml/hr with a menses simulant as detailed in the TEST METHODS section above.

Figure 15:
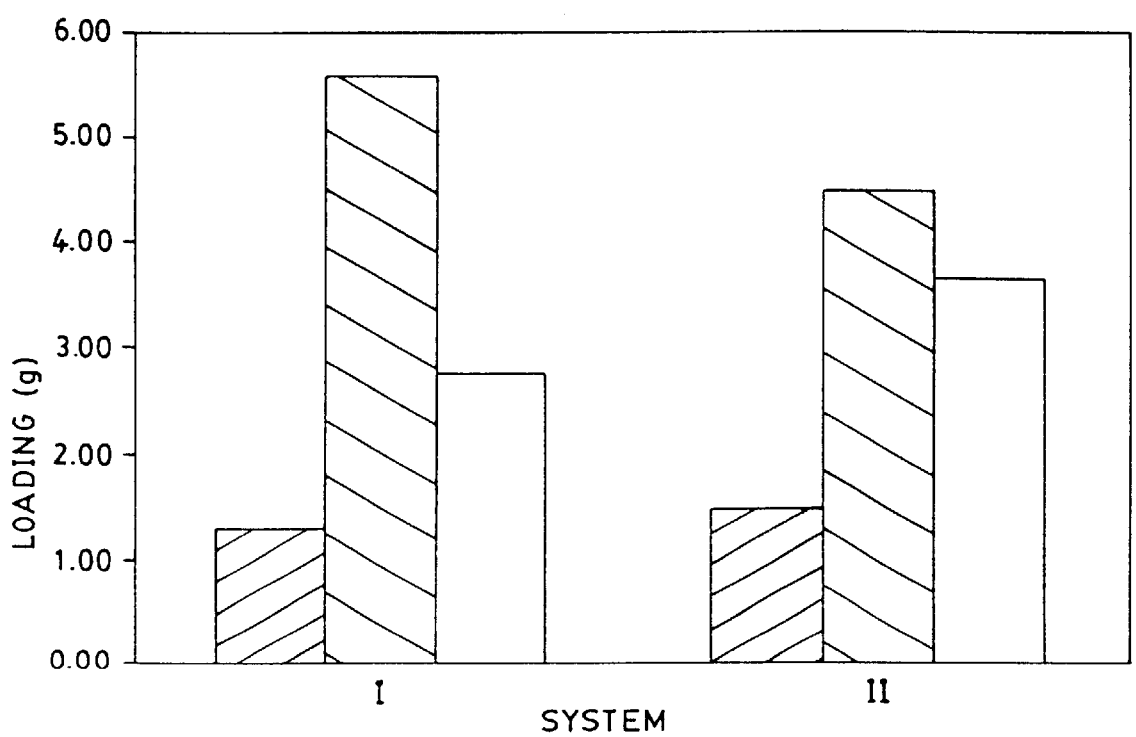
FIG. 15 is a bar graph for two systems having a top layer, a second layer which is the distribution/retention layer and a third which is the pad shaping layer. The bar chart shows the liquid loading in grams.

Two system designs were tested for fluid loading. The results are shown graphically in FIG. 15 where system I is on the left and system II on the right. In FIG. 15, the first bar for each system is the top layer, the second is the distribution/retention layer and the third is the pad shaping layer. The left hand scale is the liquid loading in grams. The fluid loading systems were made from Coosa pulp and synthetic fibers described in detail above and below in brief. It should also be noted that in any of the following tables which refer to an "hourglass" shape, it is the bottom layer which is so shaped, the other layers being rectangular.

Fluid Loading System Descriptions

| | | Basis Wt | % Pulp | % Binder | Density | Dimensions |
|---|---|---|---|---|---|---|
| System 1 | Top Layer | 100 gsm | 90% Coosa 0054 | 10% 2.8 d H-C T-255 | 0.10 g/cc | 38 mm × 152 mm |
| | Middle Layer | 200 gsm | 90% Coosa 0054 | 10% 2.8 d H-C T-255 | 0.20 g/cc | 38 mm × 152 mm hourglass - 60 mm ctr, |
| | Bottom Layer | 175 gsm | 90% Coosa 0054 | 10% 2.8 d H-C T-255 | 0.10 g/cc | 70 mm lobes, 218 mm long |
| System II | Top Layer | 125 gsm | 90% Rayonier 9401 | 10% 1.7 d Danaklon | 0.10 g/cc | 38 mm × 152 mm |
| | Middle Layer | 250 gsm | 90% Rayonier 9401 | 10% 1.7 d Danaklon | 0.20 g/cc | 38 mm × 152 mm hourglass - 60 mm ctr, |
| | Bottom Layer | 250 gsm | 80% Rayonier 9401 | 20% 1.7 d Danaklon | 0.10 g/cc | 10 mm lobes, 218 mm long |

The bars in FIG. 15 represent the average data from the fluid absorbed section of the raw data. The raw data for the graph in FIG. 15 is as follows:

| | | Fluid Loading Data | | | | | | | |
|---|---|---|---|---|---|---|---|---|---|
| | | Dry Weight | | | Wet Weight | | | Fluid Absorbed | |
| | | Top Layer | Middle Layer | Bottom Layer | Top Layer | Middle Layer | Bottom Layer | Top Layer | Middle Layer | Bottom Layer |
| System I | 1 | 0.66 | 1.37 | 2.56 | 2.02 | 6.81 | 5.21 | 1.36 | 5.44 | 2.65 |
| | 2 | 0.63 | 1.34 | 2.37 | 2.00 | 6.98 | 4.73 | 1.37 | 5.64 | 2.36 |
| | 3 | 0.59 | 1.30 | 2.73 | 1.78 | 5.98 | 6.02 | 1.19 | 4.68 | 3.29 |
| | avg | 0.63 | 1.34 | 2.55 | 1.93 | 6.59 | 5.32 | 1.31 | 5.25 | 2.77 |
| System II | 1 | 0.64 | 1.55 | 3.19 | 2.45 | 5.82 | 7.02 | 1.81 | 4.27 | 3.83 |
| | 2 | 0.65 | 1.70 | 3.45 | 2.32 | 5.96 | 7.30 | 1.67 | 4.26 | 3.85 |
| | 3 | 0.64 | 1.61 | 3.26 | 1.99 | 6.41 | 6.77 | 1.35 | 4.80 | 3.51 |
| | 4 | 0.64 | 1.67 | 3.52 | 1.98 | 6.17 | 7.33 | 1.34 | 4.50 | 3.81 |
| | 5 | 0.72 | 1.58 | 3.33 | 2.32 | 6.17 | 6.64 | 1.60 | 4.59 | 3.31 |
| | 6 | 0.68 | 1.52 | 3.50 | 1.92 | 6.09 | 7.05 | 1.24 | 4.57 | 3.55 |
| | avg | 0.66 | 1.61 | 3.38 | 2.16 | 6.10 | 7.02 | 1.50 | 4.50 | 3.64 |

A stain size ratio is useful in describing the components and system of this invention. The strain size ratio is defined as the width of the stain (w) divided by the length of the stain (l) after the stain has reached equilibrium. The pad shaping layer and distribution/retention layers must have stain size ratios less than or equal to 0.5, more particularly 0.375 and still more particularly 0.1875. Samples having a length of 8.7 inches for the pad shaping layer and 6 inches for the distribution/retention layer were tested, though it should be noted that longer or shorter products having these ratio are intended to be within the scope of this invention. Below is a description of layer of the systems tested and the data follows immediately after the description. Note that system I is the same as the previous system I.

| | | Stain Length System Descriptions | | | | |
|---|---|---|---|---|---|---|
| | | Basis Wt | % Pulp | % Binder | Density | Dimensions |
| System I | Top Layer | 100 gsm | 90% Coosa 0054 | 10% 2.8 d H-C T-255 | 0.10 g/cc | 38 mm × 152 mm |
| | Middle Layer | 200 gsm | 90% Coosa 0054 | 10% 2.8 d H-C T-255 | 0.20 g/cc | 38 mm × 152 mm hourglass - 60 mm ctr, |
| | Bottom Layer | 175 gsm | 90% Coosa 0054 | 10% 2.8 d H-C T-255 | 0.10 g/cc | 70 mm lobes, 218 mm long |
| System III | Top Layer | 25 gsm | | 100% 3.0 d Chisso ESC- | 0.03 g/cc | 38 mm × 152 mm |
| | Middle Layer | 175 gsm | 90% Coosa 0054 | 10% 2.8 d H-C T-255 | 0.20 g/cc | 38 mm × 152 mm hourglass - 60 mm ctr, |
| | Bottom Layer | 200 gsm | 90% Coosa 0054 | 10% 2.8 d H-C T-255 | 0.10 g/cc | 70 mm lobes, 218 mm long |

| | | Stain Length and Ratio Data | | | | | | | |
|---|---|---|---|---|---|---|---|---|---|
| | | Stain Length | | | Stain Width | | | Stain Ratio | | |
| | | Top Layer | Middle Layer | Bottom Layer | Top Layer | Middle Layer | Bottom Layer | Top Layer | Middle Layer | Bottom Layer |
| System I | 1 | 4.70 | 5.80 | 5.30 | 1.5 | 1.5 | 1.5 | 0.32 | 0.26 | 0.28 |
| | 2 | 4.70 | 5.80 | 5.70 | 1.5 | 1.5 | 1.5 | 0.32 | 0.26 | 0.26 |
| | 3 | 5.20 | 5.90 | 5.70 | 1.5 | 1.5 | 1.5 | 0.29 | 0.25 | 0.26 |
| | avg | 4.87 | 5.83 | 5.57 | 1.5 | 1.5 | 1.5 | 0.31 | 0.26 | 0.27 |
| System III | 1 | 1.40 | 6.00 | 6.00 | 1.5 | 1.5 | 1.5 | 1.07 | 0.25 | 0.25 |
| | 2 | 1.40 | 6.00 | 6.00 | 1.5 | 1.5 | 1.5 | 1.07 | 0.25 | 0.25 |
| | 3 | 1.40 | 6.00 | 5.70 | 1.5 | 1.5 | 1.5 | 1.07 | 0.25 | 0.26 |
| | avg | 1.40 | 6.00 | 5.90 | 1.5 | 1.5 | 1.5 | 1.07 | 0.25 | 0.25 |

Stain width was 1.5" for all samples

In addition to the stain length ratio, the saturation profile for the middle or distribution/retention layer is important. By saturation profile what is meant is the location of liquid through the length of the layer. To determine saturation profile the distribution/retention strip may be divided into six equal length sections as follows:

| A | B | C | D | E | F |
|---|---|---|---|---|---| and a ratio taken of (C+D) divided by (A+F). This corresponds to the amount of liquid (in grams) in approximately the center third of the product divided by the sum of the liquid in each end sixth of the product. If the distribution/retention layer being tested is not rectangular as is the case here, the product should be divided so that the dry weight of each section is approximately the same. The saturation profile ratio of this invention must be at most about 4, more particularly less than about 2, still more particularly about 1.6 or less and even more particularly less than 1.4 (using six sections). Examples of materials used in testing saturation profile and the results of such testing follow:

Saturation Profile System Descriptions

|  |  | Basis Wt | % Pulp | % Binder | Density | Dimensions |
|---|---|---|---|---|---|---|
| System I | Top Layer | 100 gsm | 90% Coosa 0054 | 10% 2.8 dH-C T-255 | 0.10 g/cc | 38 mm × 152 mm |
|  | Middle Layer | 200 gsm | 90% Coosa 0054 | 10% 2.8 d H-C T-255 | 0.20 g/cc | 38 mm × 152 mm hourglass - 60 mm ctr, |
|  | Bottom Layer | 175 gsm | 90% Coosa 0054 | 10% 2.8 d H-C T-255 | 0.10 g/cc | 70 mm lobes, 218 mm long |
| System IV | Top Layer | 100 gsm | 90% Coosa 0054 | 10% 2.8 dH-C T-255 | 0.10 g/cc | 38 mm × 152 mm |
|  | Middle Layer | 175 gsm | 90% Coosa 0054 | 10% 2.8 d H-C T-255 | 0.20 g/cc | 38 mm × 152 mm hourglass - 60 mm ctr, |
|  | Bottom Layer | 200 gsm | 90% Coosa 0054 | 10% 2.8 d H-C T-255 | 0.10 g/cc | 70 mm lobes, 218 mm long |
| System V | Top Layer | 100 gsm | 94% Coosa 0054 | 6% 2.8 d H-C T-255 | 0.10 g/cc | 38 mm × 152 mm |
|  | Middle Layer | 200 gsm | 94% Coosa 0054 | 6% 2.8 d H-C T-255 | 0.20 g/cc | 38 mm × 152 mm hourglass - 60 mm ctr, |
|  | Bottom Layer | 200 gsm | 94% Coosa 0054 | 6% 2.8 d H-C- T-255 | 0.10 g/cc | 70 mm lobes, 218 mm long |

Middle Layer Saturation Profiles

|  |  | Section | | | | | | Ratio (C + D)/ (A + F) |
|---|---|---|---|---|---|---|---|---|
|  |  | A | B | C | D | E | F |  |
| System I | 1 | 2.24 | 4.30 | 4.34 | 4.30 | 4.17 | 3.47 | 1.51 |
|  | 2 | 2.85 | 4.60 | 4.60 | 4.51 | 4.51 | 2.81 | 1.61 |
|  | 3 | 1.40 | 4.03 | 4.54 | 4.58 | 4.35 | 1.17 | 3.55 |
|  | avg | 2.16 | 4.31 | 4.49 | 4.46 | 4.34 | 2.48 | 2.22 |
| System IV | 1 | 2.83 | 3.91 | 4.04 | 3.85 | 3.60 | 1.74 | 1.73 |
|  | 2 | 2.61 | 4.25 | 4.39 | 4.39 | 4.32 | 2.89 | 1.60 |
|  | 3 | 2.47 | 4.05 | 3.99 | 4.24 | 4.05 | 2.85 | 1.55 |
|  | avg | 2.64 | 4.07 | 4.14 | 4.16 | 3.99 | 2.49 | 1.62 |
| System V | 1 | 3.32 | 3.94 | 4.09 | 4.28 | 4.23 | 2.94 | 1.34 |
|  | 2 | 3.20 | 3.77 | 3.91 | 4.06 | 4.15 | 2.87 | 1.31 |
|  | 3 | 3.61 | 4.33 | 4.57 | 4.47 | 4.04 | 2.07 | 1.59 |
|  | avg | 3.38 | 4.01 | 4.19 | 4.27 | 4.14 | 2.63 | 1.41 |

A desing for a thick product was also tested for saturation profile. The design information saturation ratio data are below:

|  |  | Basis Wt | % Pulp | % Binder | Density | Dimensions |
|---|---|---|---|---|---|---|
| System I | Top Layer | 100 gsm | 90% Coosa 0054 | 10% 2.8 d H-C T-255 | 0.06 g/cc | 38 mm × 140 mm |
|  | Second Layer | 250 gsm | 90% Coosa 0054 | 10% 2.8 d H-C T-255 | 0.12 g/cc | 38 mm × 140 mm |
|  | Third Layer | 100 gsm | 90% Coosa 0054 | 10% 2.8 d H-C T-255 | 0.06 g/cc | 52 mm × 154 mm hourglass - 60 mm ctr, 70 mm lobes, 200 mm long |
|  | Bottom Layer | 470 gsm | 100% Coosa 0054 | 0% |  |  |

|   | Saturation Profile Data | | | | | Ratio | |
|---|------|------|------|------|------|------|------|
|   | A | B | C | D | E | C/A | C/E |
| 1 | 4.04 | 6.69 | 6.35 | 6.24 | 2.99 | 1.57 | 2.12 |
| 2 | 2.62 | 6.17 | 6.36 | 6.07 | 3.67 | 2.42 | 1.73 |
| avg | 3.33 | 6.43 | 6.35 | 6.15 | 3.33 | 2.00 | 1.93 |

The above Example 5 describes a feminine care pad with a transfer delay function. In Example 5 the transfer delay material has a lower density than the layer below it and therefore delays liquid transfer to the bottom layer. While material density is one way to cause the transfer of fluid to be delayed to the lower layer, other material attributes can also cause delay of fluid transfer. Other material candidates that are effective at causing delay include nonwovens such as spunbond, conjugate spunbond, or bonded carded webs. Apertured films can also be used to supply this function in an absorbent system.

When either nonwovens or films are utilized as the transfer delay material, it is preferable for them to be nonwettable. In the case of the spunbond, conjugate spunbond and film materials, the structures used in the following Examples are somewhat "flat". In other words, they do not necessarily have a lower density than the layer below them in the absorbent system design. They function by providing an partially occlusive, hydrophobic layer that begins to transfer fluid after the layer above it becomes very highly saturated.

In the Example that utilizes the bonded carded web, transfer delay also functions best when the web is hydrophobic. However, with this material both density and hydrophobicity play a role in delaying transfer.

The following Examples include six thin absorbent systems and seven thick absorbent systems that utilize various transfer delay materials. The test data illustrates that by using these materials, better saturation profile ratios can be achieved, and in some cases better stain length ratios can be achieved compared to the original designs that are based on density/pore gradients.

While the test data utilizes specific materials, other materials that are hydrophobic or materials that are hydrophobic in combination with a lower density than the material below it, can provide the transfer delay function.

An additional point regarding this data is that all preceding data divided the distribution strip into six equal sections, and this is the method used in the claims below. The following data divides the strips into five equal sections as illustrated below so that the insult point is not exactly on the dividing line between two sections. The saturation profile ratios can be calculated from both sets of data. In the case where five sections is used the saturation profile is calculated as the ratio of the amount of liquid in the center section to the sum of the end sections.

Thin Saturation Profiles with Transfer Delay Layers
A B C D E
C/((A + E)/2)
Top Layer Saturation Profiles (g/g)

|   |   | Section | | | | | Ratio |
|---|---|------|------|------|------|------|------|
|   |   | A | B | C | D | E | C/((A + E)/2) |
| System 1 | 1 | 5.58 | 5.85 | 5.68 | 6.15 | 5.51 | 1.024 |
|   | 2 | 5.48 | 5.82 | 5.51 | 5.26 | 5.19 | 1.032 |
|   | Avg | 5.53 | 5.83 | 5.59 | 5.70 | 5.35 | 1.028 |
| System 2 | 1 | 5.90 | 5.97 | 6.01 | 5.65 | 5.62 | 1.043 |
|   | 2 | 5.04 | 5.36 | 5.56 | 5.23 | 5.07 | 1.099 |
|   | Avg | 5.47 | 5.67 | 5.78 | 5.44 | 5.35 | 1.071 |
| System 3 | 1 | 5.51 | 5.88 | 5.68 | 5.58 | 5.58 | 1.024 |
|   | 2 | 5.70 | 5.81 | 5.81 | 5.84 | 5.35 | 1.052 |
|   | Avg | 5.61 | 5.84 | 5.74 | 5.71 | 5.47 | 1.038 |
| System 4 | 1 | 4.99 | 6.41 | 5.74 | 5.88 | 5.42 | 1.103 |
|   | 2 | 5.57 | 6.03 | 5.68 | 5.96 | 5.47 | 1.028 |
|   | Avg | 5.28 | 6.22 | 5.71 | 5.92 | 5.44 | 1.066 |
| System 5 | 1 | 4.51 | 5.68 | 5.75 | 5.50 | 5.28 | 1.174 |
|   | 2 | 4.87 | 5.63 | 5.63 | 5.92 | 5.34 | 1.102 |
|   | Avg | 4.69 | 5.65 | 5.69 | 5.71 | 5.31 | 1.138 |
| System 6 | 1 | 5.88 | 6.06 | 6.38 | 5.91 | 5.81 | 0.874 |
|   | 2 | 5.78 | 6.37 | 6.04 | 6.15 | 6.30 | 1.000 |
|   | Avg | 5.83 | 6.21 | 6.21 | 6.03 | 6.05 | 0.937 |

Thin Stain Length Ratios with Transfer Delay Layers
T = Top    M = Middle    B = Bottom

|   |   | Stain Length | | | Stain Width | | | Stain Ratio W/L | | |
|---|---|------|------|------|------|------|------|------|------|------|
|   |   | Layer: | | | | | | | | |
|   |   | T | M | B | T | M | B | T | M | B |
| System 1 | 1 | 6.00 | NA | 3.30 | 1.5 | NA | 1.5 | 0.25 | NA | 0.45 |
|   | 2 | 6.00 | NA | 2.00 | 1.5 | NA | 1.5 | 0.25 | NA | 0.75 |
|   | Avg | 6.00 | NA | 2.65 | 1.5 | NA | 1.5 | 0.25 | NA | 0.60 |
| System 2 | 1 | 6.00 | NA | 2.60 | 1.5 | NA | 1.5 | 0.25 | NA | 0.58 |
|   | 2 | 6.00 | NA | 4.30 | 1.5 | NA | 1.5 | 0.25 | NA | 0.35 |
|   | Avg | 6.00 | NA | 3.45 | 1.5 | NA | 1.5 | 0.25 | NA | 0.47 |
| System 3 | 1 | 6.00 | NA | 0.90 | 1.5 | NA | 1.5 | 0.25 | NA | 1.67 |
|   | 2 | 6.00 | NA | 2.10 | 1.5 | NA | 1.5 | 0.25 | NA | 0.71 |
|   | Avg | 6.00 | NA | 1.50 | 1.5 | NA | 1.5 | 0.25 | NA | 1.19 |
| System 4 | 1 | 6.00 | NA | 1.50 | 1.5 | NA | 1.5 | 0.25 | NA | 1.00 |
|   | 2 | 6.00 | NA | 1.40 | 1.5 | NA | 1.5 | 0.25 | NA | 1.07 |
|   | Avg | 6.00 | NA | 1.45 | 1.5 | NA | 1.5 | 0.25 | NA | 1.03 |
| System 5 | 1 | 5.80 | NA | 4.90 | 1.5 | NA | 1.5 | 0.26 | NA | 0.31 |
|   | 2 | 6.00 | NA | 4.10 | 1.5 | NA | 1.5 | 0.25 | NA | 0.37 |
|   | Avg | 5.90 | NA | 4.50 | 1.5 | NA | 1.5 | 0.25 | NA | 0.34 |
| System 6 | 1 | 6.00 | NA | 0.00 | 1.5 | NA | 1.5 | 0.25 | NA | infinite |
|   | 2 | 6.00 | NA | 0.00 | 1.5 | NA | 1.5 | 0.25 | NA | infinite |
|   | Avg | 6.00 | NA | 0.00 | 1.5 | NA | 1.5 | 0.25 | NA | infinite |

All thin systems comprised of:

|  | Basis Wt | % Pulp | % Binder | Density | Dimensions |
|---|---|---|---|---|---|
| Top Layer | 250 gsm | 90% Weyerheauser NB 416 | 10% 2.8 d H-C T-255 | 0.14 g/cc | 38 mm × 140 mm |
| Middle Layer | See descriptions below |  |  |  | 52 mm × 154 mm |
| Bottom Layer | 175 gsm | 88% Weyerheauser NB 416 | 12% 2.8 d H-C T-255 | 0.08 g/cc | hourglass - 60 mm ctr, 70 mm lobes, 200 m long |

Middle Transfer Delay Layers for system described above:
System 1: 27 gsm (0.8 osy), 2.2 denier polypropylene spunbond
System 2: 34 gsm (1.0 osy), 2.2 denier polypropylene spunbond
Syttem 3: 10 osy, 2.0 denier polypropylene/polyethylene side-by-side conjugate fiber
System 4: 51 gsm (1.5 osy), 2.0 denier polypropylene/polyethylene side-by-side conjugate fiber
System 5: 1.0 mil apertured polyethylene film
System 6: 50 gsm bonded carded web Thick Saturation Profiles with Transfer Delay Layers
Top Layer Saturation Profiles (g/g)

|  |  | Section | | | | | Ratio |
|---|---|---|---|---|---|---|---|
|  |  | A | B | C | D | E | C/((A + E)/2) |
| System 1 | 1 | 6.48 | 7.90 | 8.10 | 8.05 | 7.38 | 1.16 |
|  | 2 | 6.43 | 7.81 | 8.24 | 8.00 | 4.76 | 1.47 |
|  | Avg | 6.45 | 7.86 | 8.17 | 8.02 | 6.07 | 1.32 |
| System 2 | 1 | 7.24 | 7.90 | 8.24 | 8.05 | 7.52 | 1.12 |
|  | 2 | 6.98 | 8.13 | 8.09 | 8.18 | 7.46 | 1.12 |
|  | Avg | 7.11 | 8.02 | 8.16 | 8.12 | 7.49 | 1.12 |
| System 3 | 1 | 6.79 | 8.86 | 8.01 | 7.87 | 7.51 | 1.12 |
|  | 2 | 7.99 | 8.66 | 8.71 | 8.71 | 8.28 | 1.12 |
|  | Avg | 7.39 | 8.76 | 8.36 | 8.29 | 7.90 | 1.12 |
| System 4 | 1 | 7.59 | 8.22 | 7.93 | 8.66 | 8.17 | 1.00 |
|  | 2 | 8.01 | 8.55 | 8.11 | 8.50 | 7.91 | 1.02 |
|  | Avg | 7.80 | 8.39 | 8.02 | 8.58 | 8.04 | 1.01 |
| System 5 | 1 | 0.31 | 6.62 | 7.04 | 6.43 | 3.44 | 3.75 |
|  | 2 | 0.12 | 5.29 | 7.35 | 7.04 | 2.26 | 6.17 |
|  | Avg | 0.21 | 5.96 | 7.19 | 6.73 | 2.85 | 4.96 |
| System 6 | 1 | 5.31 | 5.35 | 5.22 | 5.03 | 5.57 | 0.96 |
|  | 2 | 4.82 | 5.27 | 5.01 | 5.11 | 5.27 | 0.99 |
|  | Avg | 5.07 | 5.31 | 5.12 | 5.07 | 5.42 | 0.98 |
| System 7 | 1 | 3.65 | 5.94 | 6.33 | 6.22 | 3.51 | 1.77 |
|  | 2 | 3.65 | 6.11 | 6.15 | 6.15 | 2.49 | 2.00 |
|  | Avg | 3.65 | 6.03 | 6.24 | 6.19 | 3.00 | 1.89 |

Thick Stain Length Ratios with Transfer Delay Layers

|  |  | Stain Length | | | Stain Width | | | Stain Ratio W/L | | |
|---|---|---|---|---|---|---|---|---|---|---|
|  |  | Layer: | | | | | | | | |
|  |  | T | M | B | T | M | B | T | M | B |
| System 1 | 1 | 6.00 | NA | 3.20 | 1.5 | NA | 1.5 | 0.25 | NA | 0.47 |
|  | 2 | 5.60 | NA | 3.80 | 1.5 | NA | 1.5 | 0.27 | NA | 0.39 |
|  | Avg | 5.80 | NA | 3.50 | 1.5 | NA | 1.5 | 0.26 | NA | 0.43 |
| System 2 | 1 | 6.00 | NA | 1.50 | 1.5 | NA | 1.5 | 0.25 | NA | 1.00 |
|  | 2 | 6.00 | NA | 2.50 | 1.5 | NA | 1.5 | 0.25 | NA | 0.60 |
|  | Avg | 6.00 | NA | 2.00 | 1.5 | NA | 1.5 | 0.25 | NA | 0.80 |
| System 3 | 1 | 6.00 | NA | 0.50 | 1.5 | NA | 1.5 | 0.25 | NA | 3.00 |
|  | 2 | 6.00 | NA | 1.50 | 1.5 | NA | 1.5 | 0.25 | NA | 1.00 |
|  | Avg | 6.00 | NA | 1.00 | 1.5 | NA | 1.5 | 0.25 | NA | 2.00 |
| System 4 | 1 | 6.00 | NA | 1.50 | 1.5 | NA | 1.5 | 0.25 | NA | 1.00 |
|  | 2 | 6.00 | NA | 1.00 | 1.5 | NA | 1.5 | 0.25 | NA | 1.50 |
|  | Avg | 6.00 | NA | 1.25 | 1.5 | NA | 1.5 | 0.25 | NA | 1.25 |
| System 5 | 1 | 5.30 | NA | 4.20 | 1.5 | NA | 1.5 | 0.28 | NA | 0.36 |
|  | 2 | 4.60 | NA | 3.70 | 1.5 | NA | 1.5 | 0.33 | NA | 0.40 |
|  | Avg | 4.95 | NA | 3.95 | 1.5 | NA | 1.5 | 0.31 | NA | 0.38 |
| System 6 | 1 | 6.00 | NA | 0.50 | 1.5 | NA | 1.5 | 0.25 | NA | 3.00 |
|  | 2 | 6.00 | NA | 0.70 | 1.5 | NA | 1.5 | 0.25 | NA | 2.14 |
|  | Avg | 6.00 | NA | 0.60 | 1.5 | NA | 1.5 | 0.25 | NA | 2.57 |
| System 7 | 1 | 4.7 | 4.4 | 2.0 | 1.5 | 1.5 | 1.5 | 0.32 | 0.34 | 0.75 |
|  | 2 | 4.8 | 3.7 | 1.7 | 1.5 | 1.5 | 1.5 | 0.31 | 0.41 | 0.88 |
|  | Avg | 4.75 | 4.05 | 1.85 | 1.5 | 1.5 | 1.5 | 0.31 | 0.38 | 0.82 |

All Thick systems comprised of:

|  | Basis Wt | % Pulp | % Binder | Density | Dimensions |
|---|---|---|---|---|---|
| Top Layer | 250 gsm | 90% Weyerhaeuser NB416 | 10% 2.8 d H-C T-255 | 0.12 g/cc | 38 mm × 140 mm |
| Middle Layer | See descriptions below |  |  |  | 52 mm × 154 mm |
| Bottom Layer | 435 gsm | 100% Coosa 0054 sinewave embossed | 0% |  | hourglass - 60 mm ctr, 70 mm lobes, 200 m long |

Middle Transfer Delay Layers for systems described above:

System 1: 0.8 osy, 2.2 denier polypropylene spunbond

System 2: 1.0 osy, 2.2 denier polypropylene spunbond

System 3: 1.0 osy, 2.0 denier polypropylene/polyethylene conjugate fiber

System 4: 1.5 osy, 2.0 denier polypropylene/polyethylene conjugate fiber

System 5: 1.0 mil apertured polyethylene film

System 6: 50 gsm bonded carded web

System 7: 100 gsm, 0.03 g/cc, 50/50 blend of Weyerhaeuser NB 416 pulp and H-C T-255 binder fiber, made according to the airlaid process.

Embodiments of personal care products encompassed by this invention include feminine hygiene pads having a body side liner, a distribution/retention layer, a transfer delay layer, a pad shaping or secondary absorbent layer, and a backsheet. The materials could be held together by various means, including adhesively, mechanically, and by thermal bonding means.

The liner may be a nonwoven fabric or a laminate of nonwoven fabric and film. If a laminate, the liner must be apertured in some manner to allow the passage of fluids. A satisfactory nonwoven for such a laminate is made from a through air bonded conjugate polypropylene/low density polyethylene, 50/50 core/sheath concentric 6 to 10 denier fibers having a finish to yield wettability. A suitable nonwoven could have a density of about 0.03 g/cc and a basis weight of about 0.7 osy (24 gsm). A suitable film for such a laminate is one such as that available from Edison Plastics, which is a film comprising 94 percent Rexene® low density polyethylene having a melt index of 5.5 and a density of 0.923 g/cc and 6 percent Ampacet® titanium dioxide concentrate. The film and nonwoven may be laminated with thermal bond pattern having, for example, an 8 to 12 percent bond area and apertured to yield about a 27 percent open area for passage of fluids.

The liner layer may be joined to the distribution/retention layer with an adhesive such as National Starch NS34-5610 or equivalent at an add-on amount of about 5 gsm. Any adhesive or other method of binding must, of course, not block fluid flow between the layers.

The distribution/retention layer may be made by the airlaid process and include, for example, 90 percent Weyerhaeuser's NB-416 or NF-405 southern softwood pulp and 10 percent Hoechst-Celanese T-255 polyethylene terephthalate/co-polyolefin, 50/50 core/sheath, concentric 2.8 denier fibers. The basis weight of the distribution layer could be about 250 gsm with a density of about 0.14 g/cc. The distribution/retention layer may be slit longitudinally as described above so that the product will arch upwards in use, improving body conformity. Such slits may be continuous or intermittent and may be centered on the product.

A suitable transfer delay layer could be a fabric made, for example, by the spunbond process from polyolefin fibers, such as polypropylene, at a basis weight of about 0.8 osy with 2.7 denier fibers. This layer could be larger in the x-y plane than the distribution layer and have a color other than white to indicate to the wearer if fluid had moved beyond the edges of the distribution/retention layer. One such color could be a rose color to provide aesthetic appeal to the product.

Once fluid retention is maximized in the distribution/retention layer and/or compressive force is exerted on the product, the transfer delay layer would allow fluid to move in the Z direction (downward) to the pad shaping layer.

The pad shaping or secondary absorbent layer could be made from the same material in the same ratios as the distribution layer but at a lower density, for example, around 0.08 g/cc and at a lower basis weight, for example, around 175 gsm. A suitable pad shaping layer could have a longitudinal embossing pattern which could serve to channel and direct fluid in a longitudinal direction so that it would not escape laterally and could enhance body conformance.

Figure 16:
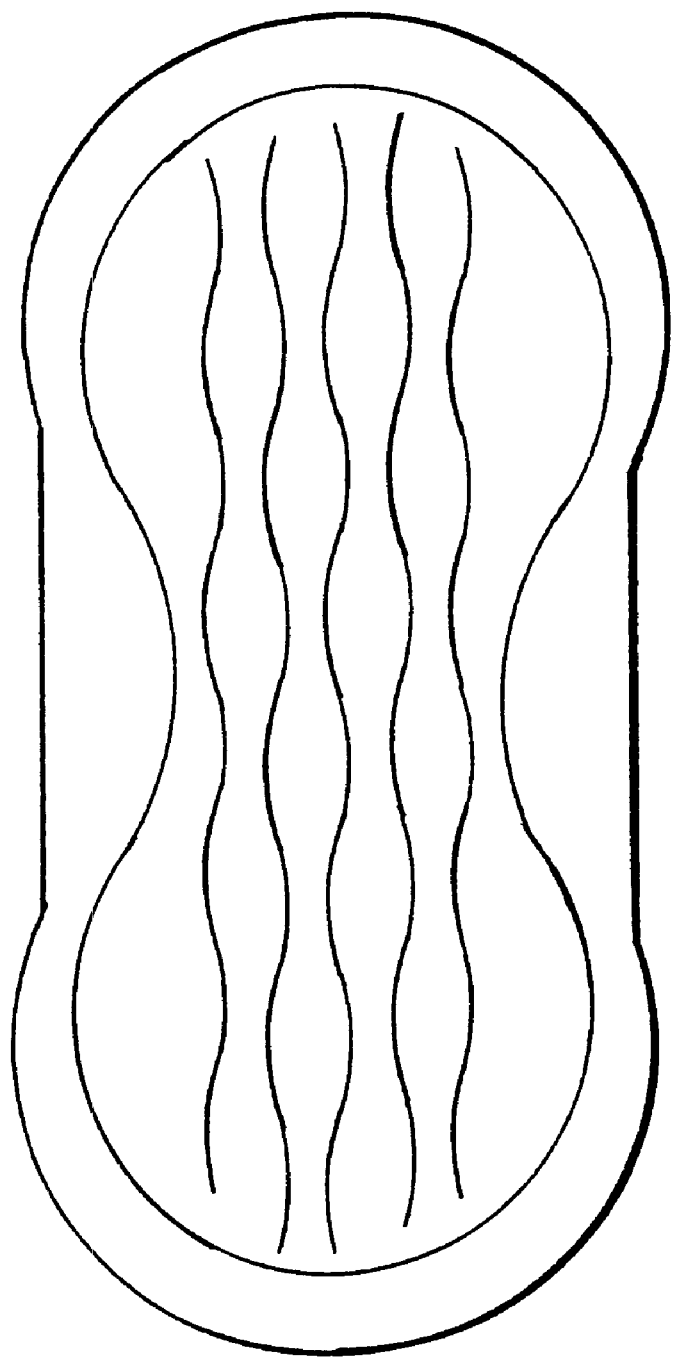
FIG. 16 shows a design for a feminine hygiene product including a sine wave pattern.

An alternate and also suitable pad shaping layer could have two layers of pulp. One such a layer could have 500 gsm of 100 percent southern softwood like Coosa 0054, Weyerhauser NB-416 or NF-405 or Georgia Pacific Golden Isles grade 4821 pulp, in a length of about 200 mm and a width of about 60–70 mm and may have, for example, a sine wave pattern as shown in FIG. 16 or another longitudinal embossing pattern. Another layer could be 400 gsm of the same materials in a length of about 160 mm and width of about 45 mm and may have an acorn or other embossing pattern.

The pad shaping layer may be adhered to the backing or baffle layer by an adhesive such as National Starch NS34-5610 in an amount less than about 15 gsm.

The backing or baffle of the product could be made from a low density, 1 mil, polyethylene film such as Edison Plastic's XP 746A rose colored, micro embossed film. Any other color may be chosen for the backing as well.

A more extensive discussion of the process and apparatus used to produce the invention may be found in a co-assigned, copending patent application under attorney docket no. 13817.

Figure 17:
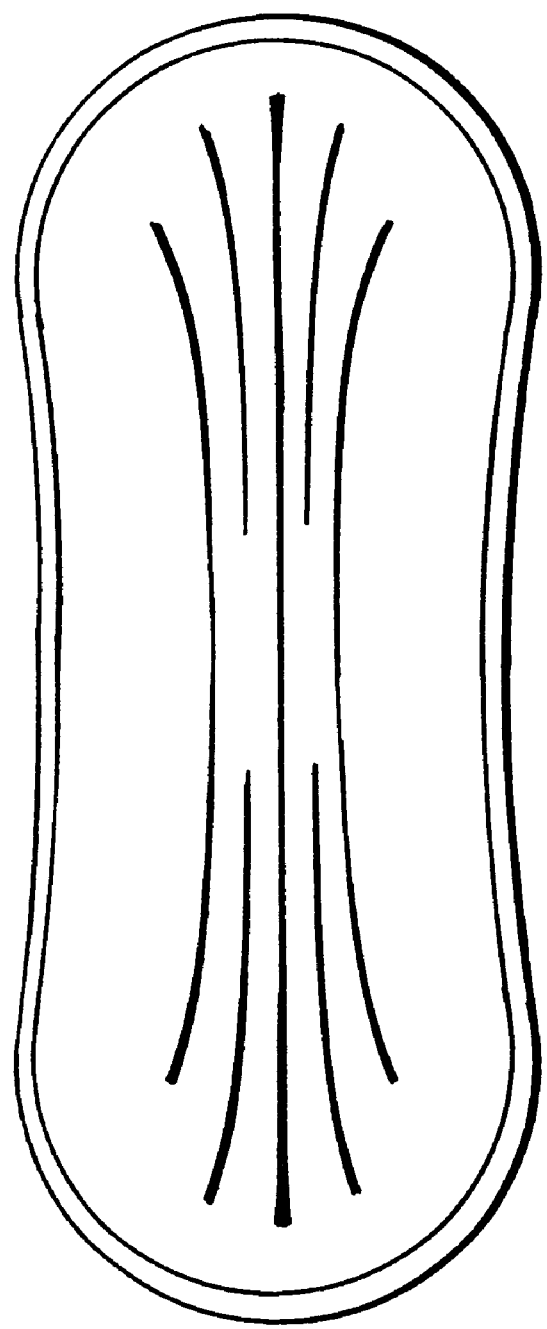
FIG. 17 shows an embossing pattern for a personal care product which is a shell pattern.

As discussed previously the entire material may be embossed, preferably from the body side liner side. The embossing could be light enough to only emboss the body side liner or could include other layers as well. The embossing pattern could be chosen to maximize material densification, which enhances fluid intake and dispersion throughout the product, and fluid distribution along the front to back axis. Embossing can also provide visual signals to the wearer that the product capacity is approaching full and should be discarded, and can be used to give an aesthetic benefit as well. Examples of suitable embossing patterns are given in the drawings. FIG. 16 is an embossing pattern for a personal care product referred to as a sine wave pattern and FIG. 17 is an embossing pattern for a personal care product referred to as a shell pattern.

It is clear that feminine personal care product systems like feminine hygiene products having the attributes required in this invention result in spreading of an insult quite well. This spreading should more efficiently utilize the entire product before leakage and so result in superior comfort for the wearer.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means plus function claims are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. A personal care product system comprising a distribution/retention layer and a pad shaping layer wherein each layer has a stain length ratio of 0.5 or less and said distribution/retention layer has a saturation profile of 4 or less, a density between 0.1 and 0.2 g/cc and an average pore size diameter of about 40 to 500 microns.

2. The personal care product system of claim 1 wherein said distribution/retention layer and said pad shaping layer each have a stain length ratio of 0.375 or less.

3. The personal care product system of claim 1 wherein said distribution/retention layer and said pad shaping layer each have a stain length ratio of 0.1875 or less.

4. The personal care product system of claim 1 wherein said distribution/retention layer has a saturation profile ratio of 2 or less.

5. The personal care product system of claim 1 wherein said distribution/retention layer has a saturation profile ratio of 1.4 or less.

6. The personal care product system of claim 1 wherein said distribution/retention layer has a density of between about 0.1 g/cc and about 0.2 g/cc.

7. The personal care product system of claim 6 wherein said distribution/retention layer has a basis weight of between about 175 and 300 gsm.

8. The personal care product system of claim 1 wherein said pad shaping layer has a density of between about 0.03 g/cc and about 0.1 g/cc.

9. The personal care product system of claim 1 wherein said pad shaping layer has a greater pore size than said distribution/retention layer.

10. The personal care product system of claim 1 further comprising an intake layer.

11. The personal care product system of claim 10 wherein said pad shaping layer has a greater pore size than said distribution/retention layer which has a lower pore size than said intake layer.

12. The personal care product system of claim 10 wherein said layers are regions of a monolithic material.

13. The personal care product system of claim 10 wherein at least one of said layers has slits.

14. The personal care product system of claim 10 wherein at least one layer is made according to a process selected from the group consisting of airlaying, wetlaying and bonded carded web processes.

15. The personal care product system of claim 14 wherein at least one layer is made from materials selected from the group consisting of cellulosic fibers, foams, synthetic fibers and mixtures thereof.

16. The personal care product system of claim 10 further comprising a transfer delay layer.

17. The personal care product system of claim 10 wherein at least one layer is embossed.

18. The personal care product system of claim 17 wherein said pad shaping layer is embossed with a sine wave pattern.

19. The personal care product system of claim 17 wherein all layers together are embossed with a shell pattern.

20. A feminine hygiene product comprising the system of claim 1.

* * * * *